(12) United States Patent
Anselm et al.

(10) Patent No.: US 7,601,752 B2
(45) Date of Patent: Oct. 13, 2009

(54) PYRROLIDINE DERIVATIVES

(75) Inventors: Lilli Anselm, Binzen (DE); Katrin Groebke Zbinden, Liestal (CH); Wolfgang Haap, Loerrach (DE); Hans Hilpert, Muenchenstein (CH); Jacques Himber, Guebwiller (FR); Bernd Kuhn, Liestal (CH); Narendra Panday, Munich (DE); Fabienne Ricklin, Hombourg (FR); Stefan Thomi, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 514 days.

(21) Appl. No.: 11/593,821

(22) Filed: Nov. 6, 2006

(65) Prior Publication Data
US 2007/0112001 A1 May 17, 2007

(30) Foreign Application Priority Data
Nov. 16, 2005 (EP) .................................. 05110818

(51) Int. Cl.
*A61K 31/4025* (2006.01)
*C07D 409/12* (2006.01)

(52) U.S. Cl. ...................... 514/423; 548/517; 548/527; 514/408; 514/422

(58) Field of Classification Search ................ 548/517, 548/527; 514/408, 422, 423
See application file for complete search history.

(56) References Cited

U.S. PATENT DOCUMENTS

| 6,642,228 | B1 | 11/2003 | Hayashi et al. |
| 7,300,929 | B2 * | 11/2007 | Baxter et al. ................ 514/218 |
| 2006/0183739 | A1 | 8/2006 | Tsaklakidis et al. |
| 2006/0183742 | A1 | 8/2006 | Mederski et al. |
| 2006/0252837 | A1 | 11/2006 | Ohta et al. |

FOREIGN PATENT DOCUMENTS

| JP | 2004210716 | 7/2004 |
| WO | WO 98/35957 | 8/1998 |
| WO | WO 00/78716 | 12/2000 |
| WO | WO 02/22575 A1 | 3/2002 |
| WO | WO 02/096873 | 12/2002 |
| WO | WO 03/045912 | 6/2003 |
| WO | WO 03/063797 | 8/2003 |
| WO | WO 2004/058715 | 7/2004 |
| WO | WO 2004/082687 | 9/2004 |
| WO | WO 2004/087646 | 10/2004 |
| WO | WO 2004/087696 | 10/2004 |
| WO | WO 2004/110433 A1 | 12/2004 |
| WO | WO 2005/032472 | 4/2005 |
| WO | WO 2006/114401 A2 | 11/2006 |

OTHER PUBLICATIONS

Cheng et al., Biochem. Pharmacol., 22, pp. 3099-3108 (1973).
Lottenberg et al., Biochm. Biophys. Acta, 742, pp. 539-557 (1983).
Eadie, G.S., J. Biol. Chem., 146, pp. 85-93 (1942).
Misumi et al., J. Am. Chem. Soc., 107, pp. 3343-3345 (1985).
Izawa et al., Tetrahedron, 48, pp. 1573-1580 (1992).

* cited by examiner

*Primary Examiner*—Golam M Shameem
(74) *Attorney, Agent, or Firm*—George W. Johnston; Dennis P. Tramaloni; Brian C. Remy

(57) ABSTRACT

The invention is concerned with novel pyrrolidine derivatives of formula (I)

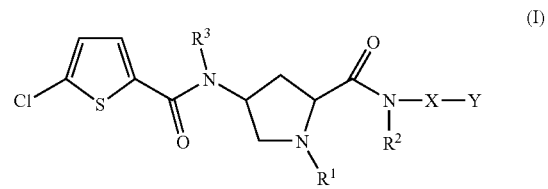

wherein X, Y, $R^1$, $R^2$ and $R^3$ are as defined in the description and in the claims, as well as physiologically acceptable salts thereof. These compounds inhibit the coagulation factor Xa and can be used as medicaments.

17 Claims, No Drawings

PYRROLIDINE DERIVATIVES

PRIORITY TO RELATED APPLICATIONS

This application claims the benefit of European Application No. 05110818.1, filed Nov. 16, 2005, which is hereby incorporated by reference in its entirety.

The invention is concerned with novel pyrrolidine derivatives of formula (I),

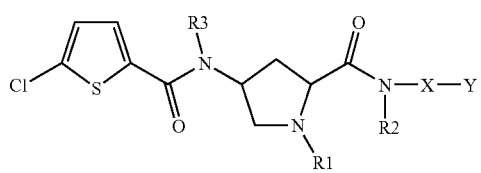

wherein
- $R^1$ is hydrogen, optionally substituted $C_{1-6}$-alkyl, optionally substituted $C_{3-7}$-cycloalkyl, optionally substituted $C_{3-7}$-cycloalkyl-$C_{1-6}$-alkyl, optionally substituted $C_{2-6}$-alkenyl, optionally substituted $C_{2-6}$-alkynyl, $R^4C(O)-$, $R^4OC(O)-$, $N(R^5,R^6)C(O)-$, $R^4OC(O)-C_{1-6}$-alkyl, $N(R^5,R^6)C(O)-C_{1-6}$-alkyl, $R^4-SO_2-$, $R^4-SO_2-C_{1-6}$-alkyl, $N(R^5,R^6)-SO_2-$, $N(R^5,R^6)-SO_2-C_{1-6}$-alkyl, heteroaryl, heteroaryl-$C_{1-6}$-alkyl, aryl, aryl-$C_{1-6}$-alkyl;
- $R^2$ is hydrogen or $C_{1-6}$ alkyl; or
- $R^1$ and $R^2$ form $C_{1-6}$ alkylene, $C_{2-7}$ alkenylene or $C_{2-7}$ alkynylene, wherein one or two $-CH_2-$ may be independently replaced with $-O-$, $-NH-$, carbonyl or $-S(O)_n-$, where n is 0, 1 or 2;
- $R^3$ is hydrogen or $C_{1-6}$ alkyl;
- $R^4$ is hydrogen, optionally substituted $C_{1-6}$-alkyl, optionally substituted $C_{3-7}$ cycloalkyl, optionally substituted $C_{3-7}$ cycloalkyl-$C_{1-6}$-alkyl, aryl, aryl-$C_{1-6}$-alkyl, heteroaryl or heteroaryl-$C_{1-6}$-alkyl;
- $R^5$ and $R^6$ independently from each other are selected from the group consisting of hydrogen, optionally substituted $C_{1-6}$-alkyl, optionally substituted $C_{3-7}$ cycloalkyl, optionally substituted $C_{3-7}$ cycloalkyl-$C_{1-6}$-alkyl, aryl, aryl-$C_{1-6}$-alkyl, heteroaryl and heteroaryl-$C_{1-6}$-alkyl; or $R^5$ and $R^6$, together with the nitrogen atom to which they are attached, form a heterocyclic ring selected from the group consisting of piperidinyl, piperazinyl, morpholinyl, pyrrolidinyl, pyrrolinyl and azetidinyl, wherein said heterocyclic ring is optionally substituted by one or more substituents independently selected from the group consisting of $C_{1-6}$-alkyl, halogen and hydroxy;
- X is arylene, heteroarylene or heterocyclylene, said arylene, heteroarylene and heterocyclylene being optionally substituted by one or more substituents independently selected from the group consisting of $C_{1-6}$ alkyl, $C_{3-7}$ cycloalkyl, $C_{3-7}$ cycloalkyl-$C_{1-6}$-alkyl, $C_{1-6}$ alkoxy, fluoro-$C_{1-6}$ alkoxy, carboxyl, halogen, cyano, nitro, amino, $-N(R')-CO-(C_{1-6}$ alkyl optionally substituted by one or more fluorine atoms), wherein R' is hydrogen, $C_{1-6}$ alkyl or fluoro $C_{1-6}$ alkyl, $-N(R')-CO-O-(C_{1-6}$ alkyl optionally substituted by one or more fluorine atoms), wherein R' is hydrogen, $C_{1-6}$ alkyl or fluoro $C_{1-6}$ alkyl, $-N(R')-CO-N(R'')(R''')$, wherein R', R'' and R''' are independently hydrogen, $C_{1-6}$ alkyl or fluoro $C_{1-6}$ alkyl, $-C(O)-N(R')(R'')$, wherein R' and R'' are independently hydrogen, $C_{1-6}$ alkyl or fluoro $C_{1-6}$ alkyl, or R' and R'', together with the nitrogen atom to which they are attached, form heterocycyl, $-NR'R''$, wherein R' and R'' are independently hydrogen, $C_{1-6}$ alkyl or fluoro $C_{1-6}$ alkyl, or R' and R'', together with the nitrogen atom to which they are attached, form heterocycyl,

wherein R' and R'' are independently $C_{1-6}$ alkyl or fluoro $C_{1-6}$ alkyl, or R' and R'', together with the nitrogen atom to which they are attached, form heterocyclyl,

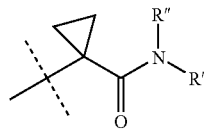

wherein R' and R'' are independently $C_{1-6}$ alkyl or fluoro $C_{1-6}$ alkyl, or R' and R'', together with the nitrogen atom to which they are attached, form heterocyclyl,

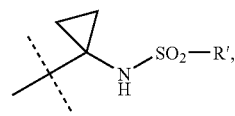

wherein R' is fluoro $C_{1-6}$ alkyl and

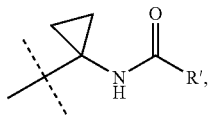

wherein R' is fluoro $C_{1-6}$ alkyl,
wherein one or two carbon atoms of said arylene, heteroarylene or heterocyclylene are optionally replaced with a carbonyl group;
Y is hydrogen, aryl, heteroaryl or heterocyclyl, wherein said aryl, heteroaryl and heterocyclyl are optionally substituted by one or more substituents independently selected from the group consisting of $C_{1-6}$ alkyl optionally substituted by one or more fluorine atoms, $C_{1-6}$ alkoxy optionally substituted by one or more fluorine atoms, halogen, cyano, nitro, amino, mono- or di-$C_{1-6}$ alkyl substituted amino, wherein $C_{1-6}$ alkyl is optionally substituted by one or more fluorine atoms, mono- or di-$C_{1-6}$ alkyl substituted amino-$C_{1-6}$ alkyl, wherein $C_{1-6}$ alkyl is optionally substituted by one or more fluorine atoms, $-SO_2-C_{1-6}$ alkyl, wherein $C_{1-6}$ alkyl is optionally substituted by one or more fluorine atoms, $-SO_2-NH_2$, $-SO_2-NH-C_{1-6}$ alkyl, wherein $C_{1-6}$ alkyl is optionally substituted by one or more fluorine atoms, and $-SO_2-N(C_{1-6}$ alkyl$)_2$, wherein $C_{1-6}$ alkyl is optionally substituted by one or more fluorine atoms, wherein one or two carbon atoms of said aryl, heteroaryl and heterocyclyl are optionally replaced with a carbonyl group;

and prodrugs and pharmaceutically acceptable salts thereof.

Further, the invention is concerned with a process and an intermediate for the manufacture of the above compounds, pharmaceutical preparations which contain such compounds, the use of these compounds for the production of pharmaceutical preparations as well as a process for the manufacture of the intermediate.

The compounds of formula (I) are active compounds and inhibit the coagulation factor Xa.

These compounds consequently influence blood coagulation. They therefore inhibit the formation of thrombi and can be used for the treatment and/or prevention of thrombotic disorders, such as amongst others, arterial and venous thrombosis, deep vein thrombosis, peripheral arterial occlusive disease (PAOD), unstable angina pectoris, myocardial infarction, coronary artery disease, pulmonary embolism, stroke (cerebral thrombosis) due to atrial fibrillation, inflammation and arteriosclerosis. They have potentially benefit in the treatment of acute vessel closure associated with thrombolytic therapy and restenosis, e.g. after transluminal coronary angioplasty (PTCA) or bypass grafting of the coronary or peripheral arteries and in the maintenance of vascular access patency in long term hemodialysis patients. F.Xa inhibitors of this invention may form part of a combination therapy with an anticoagulant with a different mode of action or with a platelet aggregation inhibitor or with a thrombolytic agent. Furthermore, these compounds have an effect on tumour cells and prevent metastases. They can therefore also be used as antitumour agents.

The present invention provides the novel compounds of formula (I) which are factor Xa inhibitors. The compounds of the present invention unexpectedly inhibit coagulation factor Xa and also exhibit improved pharmacological properties compared to other compounds already known in the art.

Unless otherwise indicated, the following definitions are set forth to illustrate and define the meaning and scope of the various terms used to describe the invention herein.

The term "halogen" or "halo" means fluorine, chlorine, bromine and iodine, with fluorine, chlorine and bromine being preferred.

The term "$C_{1-6}$ alkyl", alone or in combination with other groups, means a branched or straight-chain monovalent alkyl radical, having one to six carbon atoms. This term is further exemplified by such radicals as methyl, ethyl, n-propyl, iso-propyl, n-butyl, s-butyl, t-butyl. $C_{1-4}$ alkyl is more preferred.

The term "fluoro $C_{1-6}$ alkyl" means $C_{1-6}$ alkyl substituted by one or more, preferably one, two or three fluorine atoms.

The term "$C_{3-7}$ cycloalkyl", alone or in combination with other groups, means a saturated monovalent cyclic hydrocarbon radical of three to seven ring carbons, e.g., cyclopropyl, cyclobutyl, cyclohexyl.

The term "$C_{1-6}$ alkoxy", alone or in combination with other groups, means the group R'—O—, wherein R' is a $C_{1-6}$ alkyl.

The term "$C_{2-6}$-alkenyl", alone or in combination with other groups, means a straight-chain or branched hydrocarbon residue comprising an olefinic bond, having two to six carbon atoms, such as e.g. ethenyl, 2-propenyl.

The term "$C_{2-6}$-alkynyl", alone or in combination with other groups, means a straight-chain or branched hydrocarbon residue comprising a tripple bond, having two to six carbon atoms, such as e.g. ethynyl, 2-propynyl.

The term "optionally substituted $C_{1-6}$-alkyl", "optionally substituted $C_{3-7}$-cycloalkyl", "optionally substituted $C_{2-6}$-alkenyl" and "optionally substituted $C_{2-6}$-alkinyl" means, respectively, $C_{1-6}$-alkyl, $C_{3-7}$-cycloalkyl, $C_{2-6}$-alkenyl and $C_{2-6}$-alkinyl optionally substituted by one or more, preferably one to three substituents, independently selected from the group consisting of halogen, hydroxy and cyano, such as 2,2,2-trifluoroethyl, 2,2-difluoroethyl, 3,3,3-trifluororpopyl, 2-hydroxyethyl, cyanomethyl. For halogen, fluorine is preferred.

The term "$C_{1-6}$ alkylene" means a straight chain or branched divalent saturated aliphatic hydrocarbon group of 1 to 6 carbon atoms.

The term "$C_{2-6}$ alkenylene" means a straight-chain or branched divalent aliphatic hydrocarbon group of 2 to 6 carbon atoms, comprising an olefinic bond.

The term "$C_{2-7}$ alkynylene" means a straight-chain or branched divalent aliphatic hydrocarbon group of 2 to 6 carbon atoms, comprising a tripple bond.

The term "aryl", alone or in combination with other groups, means a phenyl or a naphthyl group, preferably a phenyl group.

The term "heterocyclyl", alone or combination with other groups, means non-aromatic mono- or bi-cyclic radicals of three to eight ring atoms wherein one or two ring atoms are heteroatoms selected from N, O, or $S(O)_n$ (where n is an integer from 0 to 2), the remaining ring atoms being C.

The term "heteroaryl" means a monocyclic or bicyclic radical of 5 to 12 ring atoms having at least one aromatic ring containing one, two, or three ring heteroatoms selected from N, O, and S, the remaining ring atoms being C. Preferably, the attachment point of the heteroaryl radical will be on an aromatic ring.

The term "arylene" means a divalent aryl group.

The term "phenylene", alone or in combination with other groups, means a divalent phenyl group. 1,4-phenylene is preferred.

The term "heterocyclylene", alone or combination with other groups, means a divalent heterocyclyl group as defined above.

The term "heteroarylene", alone or combination with other groups, means a divalent heteroaryl group as defined above. Preferably, the attachment point of the heteroaryl radical will be on an aromatic ring.

Preferred radicals for the chemical groups whose definitions are given above are those specifically exemplified in Examples.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) in which a COOH group is present can further form salts with bases. Examples of such salts are alkaline, earth-alkaline and ammonium salts such as e.g. Na—, K—, Ca— and Trimethylammoniumsalt. The term "pharmaceutically acceptable salts" also refers to such salts. Acid addition salts as described above are preferred.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino.

"Optional" or "optionally" means that the subsequently described event or circumstance may but need not occur, and that the description includes instances where the event or circumstance occurs and instances in which it does not. For example, "aryl group optionally substituted with an alkyl group" means that the alkyl may but need not be present, and the description includes situations where the aryl group is substituted with an alkyl group and situations where the aryl group is not substituted with the alkyl group.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

Compounds that have the same molecular Formula but differ in the nature or sequence of bonding of their atoms or the arrangement of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". An isomer of a compound which has two asymmetric carbon atoms, and differs from another isomer only in the arrangement in space with respect to the only one asymmetric carbon atom is termed an epimer of that another isomer.

The compounds of formula (I) can possess one or more asymmetric centers. Unless indicated otherwise, the description or naming of a particular compound in the specification and claims is intended to include both individual enantiomers and mixtures, racemic or otherwise, thereof, as well as individual epimers and mixture thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

While the broadest definition of this invention is described before, certain compounds of formula (I) are preferred.

i) A preferred compound of the invention is a compound of formula (I), wherein

X is phenylene, heteroarylene or heterocyclylene, said phenylene, heteroarylene and heterocyclylen being optionally substituted by one or more substituents independently selected from the group consisting of $C_{1-6}$ alkyl, $C_{1-6}$ alkoxy, halogen and cyano;

Y is phenyl, heteroaryl or heterocyclyl, said phenyl, heteroaryl and heterocyclyl being optionally substituted by one or more substituents independently selected from the group consisting of $C_{1-6}$ alkyl, $C_{1-6}$ alkoxy and halogen and one or two carbon atoms of said phenyl, heteroaryl and heterocyclyl being optionally replaced with a carbonyl group.

ii) Another preferred compound of the invention is a compound of formula (I), wherein X is phenylene, which is optionally substituted by one or more substituents independently selected from the group consisting of halogen and cyano;

Y is heteroaryl or heterocyclyl, said heteroaryl and heterocyclyl being optionally substituted by one or more same or different $C_{1-6}$ alkyl, and one or two carbon atoms of said heteroaryl and heterocyclyl being optionally replaced with a carbonyl group.

iii) Another preferred compound of the invention is a compound of formula (I), wherein X is 1,4-phenylene optionally substituted by one to three, preferably one substituent selected from the group consisting of halogen, preferably fluorine, and cyano.

iv) Another preferred compound of the invention is a compound of formula (I), wherein X is 1,4-phenylene, 2-fluoro-1,4-phenylene or 2-cyano-1,4-phenylene.

v) Another preferred compound of the invention is a compound of formula (I), wherein Y is heteroaryl or heterocyclyl, said heteroaryl and heterocyclyl being a mono-cyclic radical of six ring atoms in which one or two ring atoms are heteroatoms selected from N and O, the remaining ring atoms being C, and one carbon atoms of said heteroaryl and heterocyclyl being replaced with a carbonyl group.

vi) Another preferred compound of the invention is a compound of formula (I), wherein Y is pyridyl, pyrazinyl or morpholinyl, one carbon atoms of said pyridyl, pyrazinyl and morpholinyl being replaced with a carbonyl group.

vii) Another preferred compound of the invention is a compound of formula (I), wherein Y is 2-oxo-1-pyridyl, 2-oxo-1-pyrazinyl or 3-oxo-4-morpholinyl.

viii) Another preferred compound of the invention is a compound of formula (I), wherein $R^1$ is hydrogen, optionally substituted $C_{1-6}$-alkyl, $R^4C(O)$—, $R^4OC(O)$—, $R^4OC(O)$—$C_{1-6}$-alkyl, $R^4$—$SO_2$— or $R^4$—$SO_2$—$C_{1-6}$-alkyl, in which $R^4$ is hydrogen or optionally substituted $C_{1-6}$-alkyl.

ix) Another preferred compound of the invention is a compound of formula (I), wherein $R^1$ is hydrogen, optionally substituted $C_{1-6}$-alkyl, $R^4OC(O)$— or $R^4OC(O)$—$C_{1-6}$-alkyl, in which $R^4$ is $C_{1-6}$-alkyl.

x) Another preferred compound of the invention is a compound of formula (I), wherein $R^1$ is hydrogen or $C_{1-6}$-alkyl.

xi) Another preferred compound of the invention is a compound of formula (I), wherein $R^2$ is hydrogen or $C_{1-6}$ alkyl.

xii) Another preferred compound of the invention is a compound of formula (I), wherein $R^2$ is hydrogen.

xiii) Another preferred compound of the invention is a compound of formula (I), wherein $R^1$ and $R^2$ form $C_{1-6}$ alkylene, $C_{2-7}$ alkenylene or $C_{2-7}$ alkynylene, in which one or two —$CH_2$— may be independently replaced with —O—, —NH—, carbonyl or —$S(O)_n$—, where n is 0, 1 or 2. Preferably $R^1$ and $R^2$ form $C_{1-6}$ alkylene, in which one of —$CH_2$— is optionally replaced with —O—, —NH—, carbonyl or —$S(O)_n$—, where n is 0, 1 or 2. More preferably $R^1$ and $R^2$ form $C_{1-6}$ alkylene, in which one of —$CH_2$— is optionally replaced with carbonyl.

xiv) Another preferred compound of the invention is a compound of formula (I), wherein $R^3$ is hydrogen.

xv) Another preferred compound of the invention is a compound of formula (I), which is

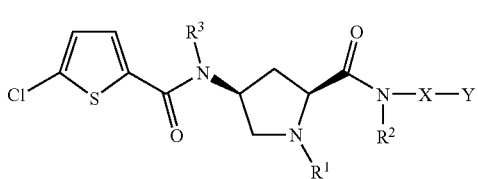

(I)

wherein X, Y, $R^1$, $R^2$ and $R^3$ are as defined before.

xvi) Another preferred compound of the invention is a compound of formula (I), wherein X is arylene, heteroarylene or heterocyclylene, said arylene, heteroarylene and heterocyclylen being optionally substituted by one or more substituents independently selected from the group consisting of $C_{1-6}$ alkyl, $C_{3-7}$ cycloalkyl, $C_{3-7}$ cycloalkyl-$C_{1-6}$-alkyl, $C_{1-6}$ alkoxy, fluoro-$C_{1-6}$ alkoxy, halogen, cyano, nitro, amino, —N(R')—CO—($C_{1-6}$ alkyl optionally substituted by one or more fluorine atoms), in which R' is hydrogen, $C_{1-6}$ alkyl or fluoro $C_{1-6}$ alkyl, —N(R')—CO—O—($C_{1-6}$ alkyl optionally substituted by one or more fluorine atoms), in which R' is hydrogen, $C_{1-6}$ alkyl or fluoro $C_{1-6}$ alkyl, —N(R')—CO—N(R'') (R'''), in which R', R'' and R''' are independently hydrogen, $C_{1-6}$ alkyl or fluoro $C_{1-6}$ alkyl, —C(O)—N(R')(R''), in which R' and R'' are independently hydrogen, $C_{1-6}$ alkyl or fluoro $C_{1-6}$ alkyl, or R' and R'', together with the nitrogen atom to which they are attached, form heterocycyl, —NR'R'', in which R' and R'' are independently hydrogen, $C_{1-6}$ alkyl or fluoro $C_{1-6}$ alkyl, or R' and R'', together with the nitrogen atom to which they are attached, form heterocycyl,

wherein R' and R'' are independently $C_{1-6}$ alkyl or fluoro $C_{1-6}$ alkyl, or R' and R'', together with the nitrogen atom to which they are attached, form heterocyclyl,

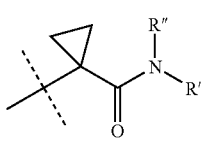

wherein R' and R'' are independently $C_{1-6}$ alkyl or fluoro $C_{1-6}$ alkyl, or R' and R'', together with the nitrogen atom to which they are attached, form heterocyclyl,

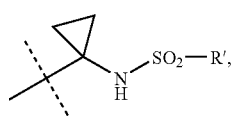

in which R' is fluoro $C_{1-6}$ alkyl and

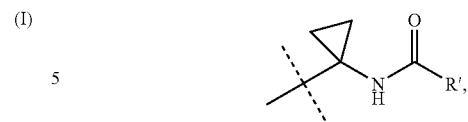

in which R' is fluoro $C_{1-6}$ alkyl, and one or two carbon atoms of said arylene, heteroarylene or heterocyclylene being optionally replaced with a carbonyl group.

xvii) Another preferred compound of the invention is a compound of formula (I), which is (2S,4S)-4-[(5-Chloro-thiophene-2-carbonyl)-amino]-pyrrolidine-2-carboxylic acid[2-fluoro-4-(2-oxo-2H-pyridin-1-yl)-phenyl]-amide trifluoro-acetate, (2S,4S)-4-[(5-Chloro-thiophene-2-carbonyl)-amino]-pyrrolidine-2-carboxylic acid[2-fluoro-4-(2-oxo-2H-pyridin-1-yl) -phenyl]-amide, (S)-4-[(5-Chloro-thiophene-2-carbonyl)-amino]-pyrrolidine-2-carboxylic acid[4-(2-oxo-2H-pyridin-1-yl)-phenyl]-amide, (S)-4-[(5-Chloro-thiophene-2-carbonyl)-amino]-1-(2-hydroxy-ethyl)-pyrrolidine-2-carboxylic acid[4-(2-oxo-2H-pyridin-1-yl)-phenyl]-amide, (2S,4S) -4-[(5-Chloro-thiophene-2-carbonyl)-amino]-pyrrolidine-2-carboxylic acid[2-fluoro-4-(2-oxo-2H-pyrazin-1-yl)-phenyl]-amide, (S)-4-[(5-Chloro-thiophene-2-carbonyl)-amino]-1-methyl-pyrrolidine-2-carboxylic acid [4-(2-oxo-2H-pyridin-1-yl)-phenyl]-amide, 3-{(2S,4S)-4-[(5-Chloro-thiophene-2-carbonyl)-amino]-2-[2-fluoro-4-(2-oxo-2H-pyridin-1-yl)-phenylcarbamoyl]-pyrrolidin-1-yl}-propionic acid ethyl ester, (S)-4-[(5-Chloro-thiophene-2-carbonyl)-amino]-2-[2-cyano-4-(2-oxo-2H-pyridin-1-yl)-phenylcarbamoyl]-pyrrolidine-1-carboxylic acid tert-butyl ester, (2S,4S)-4-[(5-Chloro-thiophene-2-carbonyl)-amino]-1-methyl-pyrrolidine-2-carboxylic acid[2-cyano-4-(3-oxo-morpholin-4-yl)-phenyl]-amide, (S)-4-[(5-Chloro-thiophene-2-carbonyl)-amino]-pyrrolidine-2-carboxylic acid[2-cyano-4-(2-oxo-2H-pyridin-1-yl)-phenyl]-amide trifluoro-acetate, or (S)-4-[(5-Chloro-thiophene-2-carbonyl)-amino]-1-methyl-pyrrolidine-2-carboxylic acid [2-cyano-4-(2-oxo-2H-pyridin-1-yl)-phenyl]-amide.

The compounds of the present invention can be prepared, for example, by the general synthetic procedures described below.

General Synthetic Procedures

Abbreviations:

Alloc: Allyloxycarbonyl
BOP: Benzotriazolyl-N-oxy-tris(dimethylamino)-phosphonium hexafluorophosphate
BOP-Cl: Bis-(2-oxo-3-oxazolidinyl)-phosphinic acid chloride
CDI: 1,1'-Carbonyldiimidazole
dba: dibenzylidenacetone
DBU: 1,8-Diazbicyclo[5.4.0]undec-7-ene.
DCC: N,N'-Dicyclohexylcarbodiimide
DIC: N,N'-Diisopropylcarbodiimide
DIEA: N,N-Diisopropylethyl amine
DMA: N,N-Dimethylacetamide
DMF: N,N-Dimethylformamide
DMSO: Dimethylsulfoxid
dppb: 1,4-bis(diphenylphosphino)butane EDC: N-(3-Dimetylaminopropyl)-N'-ethyl-carbodiimide hydrochloride
EEDQ: N-Ethoxycarbonyl-2-ethoxy-1,2-dihydroquinoline
Fmoc: 9-Fluorenylmethyloxycarbonyl
HATU: O-(7-Azabenzotriazol-1-yl)-N,N,N',N'-tetramethyluronium hexafluorophosphate
HBTU: O-(Benzotriazol-1-yl)-N,N,N',N'-tetramethyluronium hexafluorophosphate
HOBt: N-Hydroxybenzotriazole
IBCF: Isobutyl chloroformiate
LiHMDS: Lithium bis(trimethylsilyl)amide
NMM: N-Methylmorpholin
NMP: N-Methylpyrrolidone
PyBOP: Benzotriazol-1-yl-oxytripyrrolidinephosphonium hexafluorophosphate
PyBrOP: Brom-tripyrrolidinophosphonium hexafluorophosphate
TBAF: Tetrabutylammonium fluoride
TBTU: O-(Benzotriazol-1-yl)-N,N,N',N'-tetramethyluronium terafluoroborate
TEA: Triethylamin
Teoc: 2-(Trimethylsilyl)ethyloxy carbonyl
TFA: Trifluoroacetic acid
THF: Tetrahydrofurane
TPPTS: 3,3',3"-Phosphinidyne tris(benzene sulfonic acid), trisodium salt Synthesis of 4-[(5-chloro-thiophene-2-carbonyl)-amino]-pyrrolidine-2-carboxylic acid amides

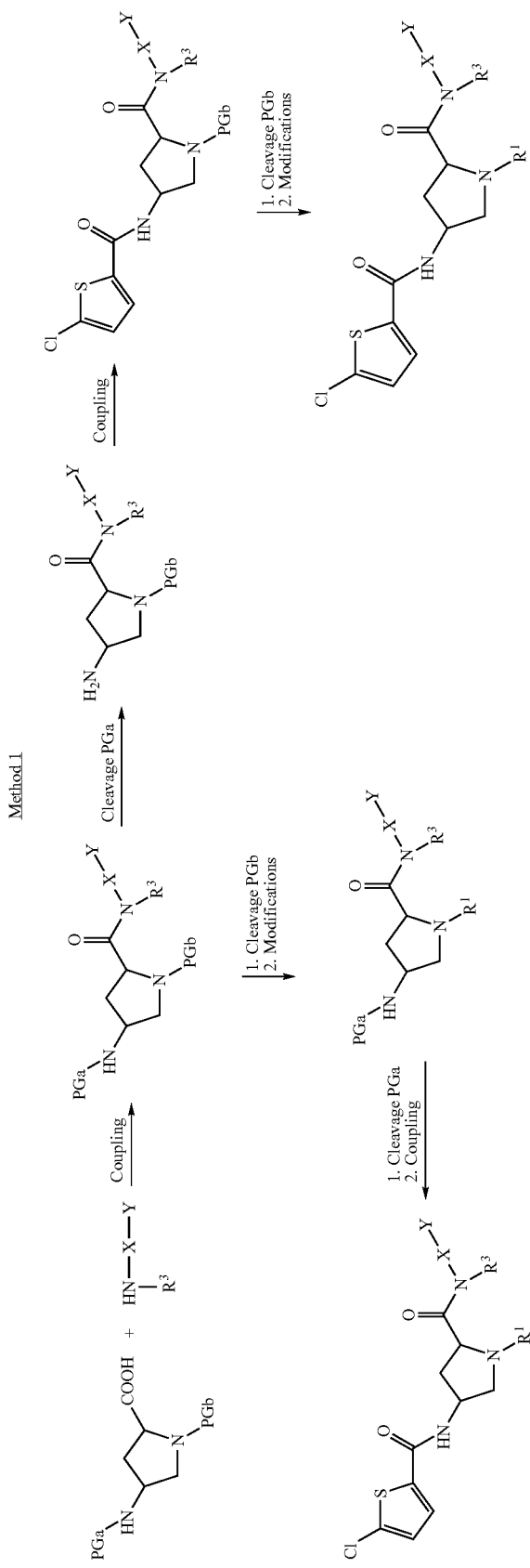

PGa and PGb are protecting groups which can be orthogonally cleaved, such as PGa/PGb being Fmoc/Boc, Fmoc/Alloc, Boc/Alloc, Benzyloxycarbonyl/Boc, Fmoc/Benzyloxycarbonyl, Teoc/Boc, Alloc/Teoc etc. $R^1$, $R^3$, X and Y are as defined before.

Method 2
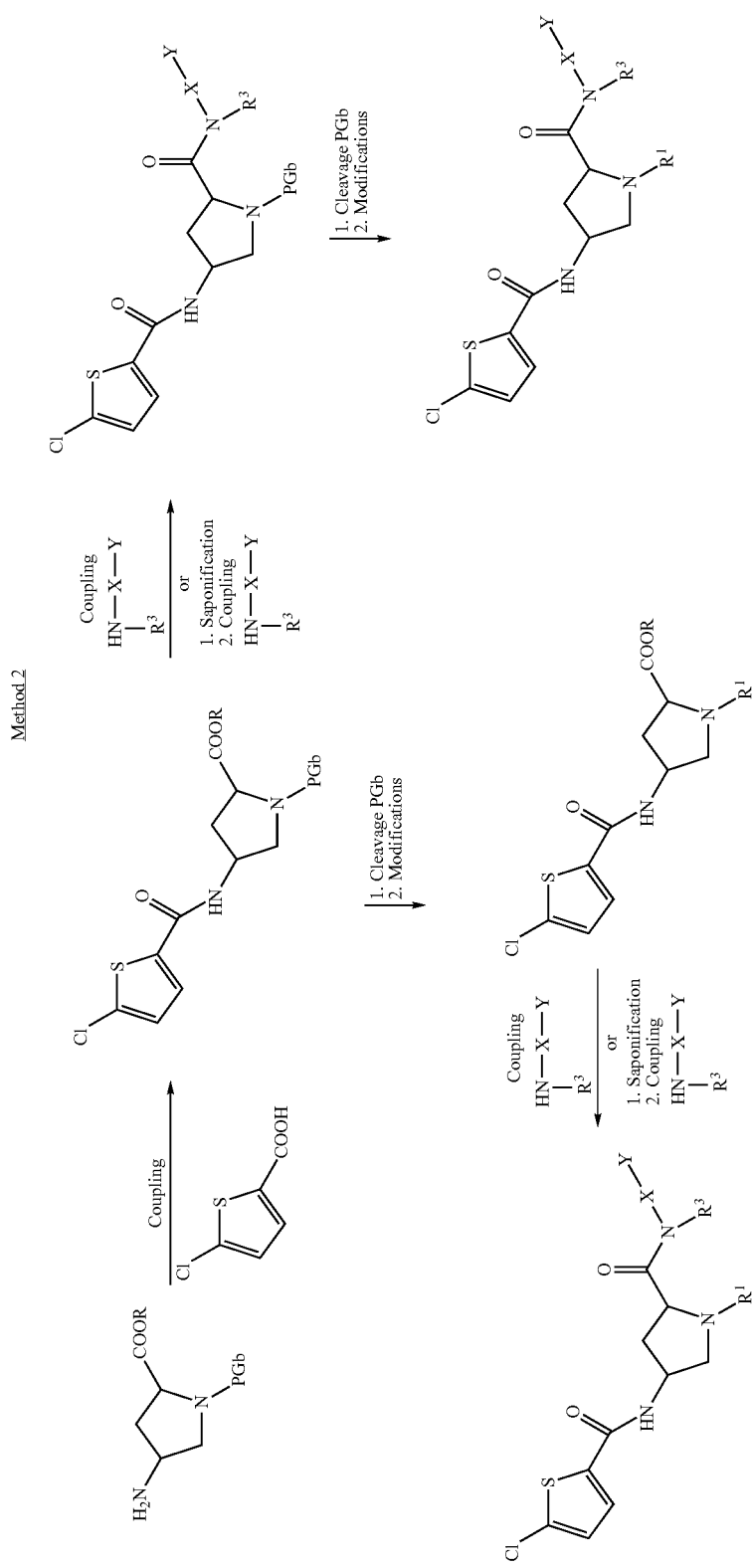

PGa and PGb are protecting groups which can be orthogonally cleaved, such as PGa/PGb being Fmoc/Boc, Fmoc/Alloc, Boc/Alloc, Benzyloxycarbonyl/Boc, Fmoc/Benzyloxycarbonyl, Teoc/Boc, Alloc/Teoc etc. R is $C_{1-6}$-alkyl, benzyl or allyl. $R^1$, $R^3$, X and Y are as defined before.

Method 3:
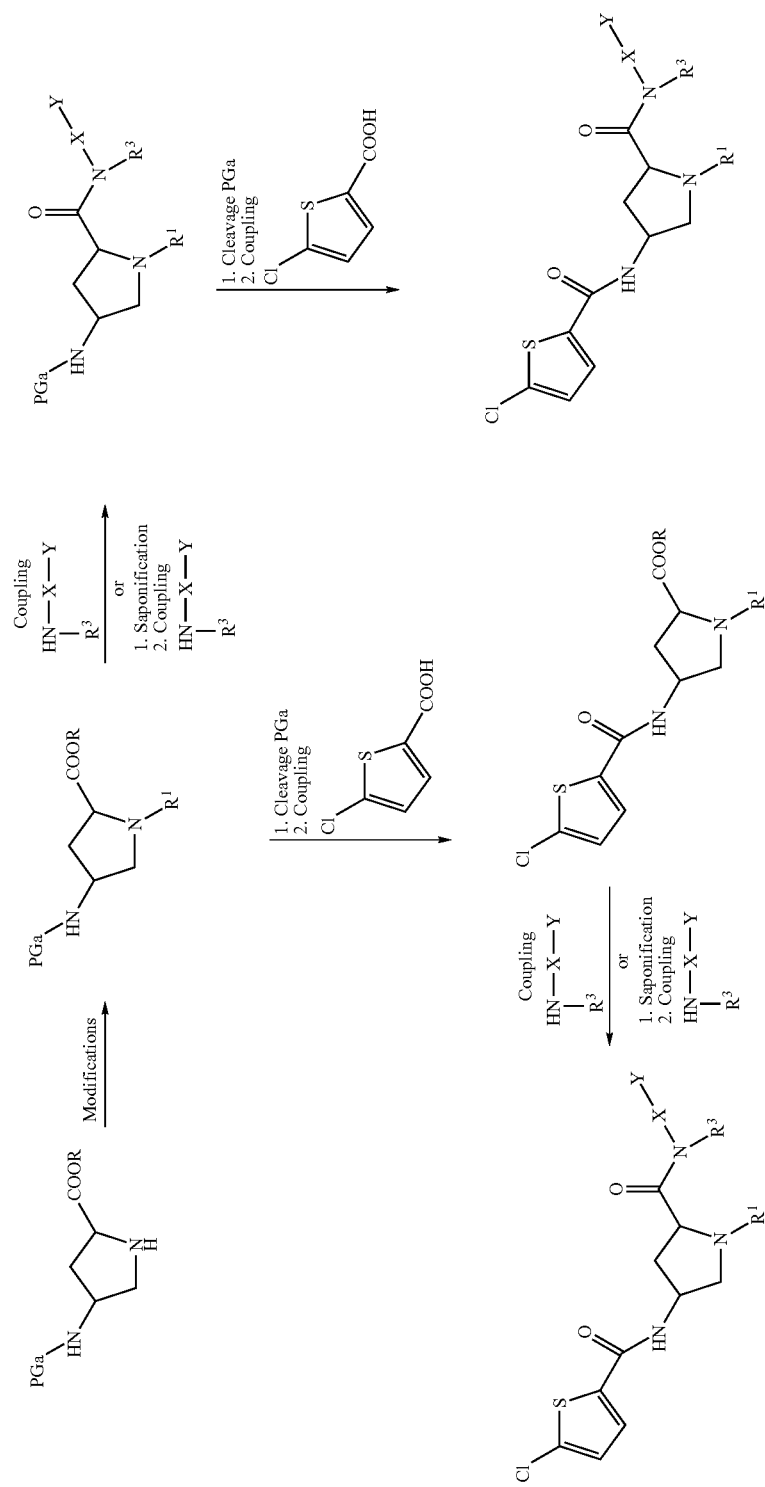

PGa and PGb are protecting groups which can be orthogonally cleaved, such as PGa/PGb being Fmoc/Boc, Fmoc/Alloc, Boc/Alloc, Benzyloxycarbonyl/Boc, Fmoc/Benzyloxycarbonyl, Teoc/Boc, Alloc/Teoc etc. R is $C_{1-6}$-alkyl, benzyl or allyl. $R^1$, $R^3$, X and Y are as defined before.

General Procedures

A: Deprotection of Amines

A1: Deprotection of a Boc-Protected Amine

Cleavage of a Boc protecting group is affected by treatment with a mineral acid such as HCl, HBr, $H_2SO_4$ or $H_3PO_4$ or a carbonic acid such as trifluoroacetic acid, in a solvent such as $CH_2Cl_2$, dioxane, EtOAc or HOAc at 0 to 60° C. Preferred conditions are 4N HCl in dioxane at r.t. or TFA in $CH_2Cl_2$ at r.t.

A2: Deprotection of an Fmoc-Protected Amine

Cleavage of an Fmoc protecting group is affected by piperidine in a solvent such as DMF, $CH_2Cl_2$, THF or dioxane at r.t.

A3: Deprotection of an Alloc-Protected Amine

Cleavage of an Alloc protecting group is affected by Pd catalysis using e.g. $Pd(PPh_3)_2Cl_2$ or $Pd(dba)_2Cl_2$, $Pd(OAc)_2$ in combination with a phosphine ligand such as dppb, TPPTS and $Bu_3SnH$, acetic acid or a base such as TEA, diethylamine in a solvent such as acetonitrile, $CH_2Cl_2$ or THF at r.t.

A4: Deprotection of a Teoc-Protected Amine

Cleavage of a Teoc protecting group is affected by TBAF in a solvent such as DMF, acetonitrile, or THF at elevated temperatures of 40-100° C.

B: Amide Coupling

Amide couplings are carried out in a solvent such as $CH_2Cl_2$, DMF, DMA, acetonitrile, THF or mixtures thereof. Activation is effected by an amide coupling reagent such as BOP, BOP-Cl, TBTU, EEDQ, EDCI, HATU, PyBOP, PyBrOP, CDI, IBCF, EDCI/DMAP and an additive such as HOBt, N-hydroxysuccinimide or N-hydroxy-2-pyridone in the presence of a base like TEA, DIPEA, N-methylmorpholine etc. at 0° C. to 100° C. Reaction times ranged from 1 hr to 72 hrs. Preferred conditions are DMF, BOP-Cl and DIPEA and IBCF, NMM in THF.

C: Conversion of a Carboxylic Acid Ester to an Aryl Amide Using $AlMe_3$ Activation The aniline is preactivated with $AlMe_3$ in a solvent such as toluene or dioxane under an argon atmosphere at r.t. for 1 hr-3 hrs and subsequently treated with the ester at elevated temperature (usually 90° C.-110° C.) for 1 hr-18 hrs to give the amide.

C': Conversion of a Carboxylic Acid Ester to an Aryl Amide Using LiHMDS Activation The aniline is preactivated with LiHMDS in a solvent such as toluene, THF or dioxane under an argon atmosphere at −10-25° C. for 1 hr-3 hrs and subsequently treated with the ester at r.t. for 1 hr-18 hrs to give the amide. Alternatively, the ester and the aniline are suspended or dissolved in a solvent such as toluene, THF or dioxane under an argon atmosphere at −10-25° C. and subsequently treated with LiHMDS for 1-18 hrs to give the amide.

D: Hydrolysis of a Carboxylic Acid Ester

Ester hydrolysis is effected by dissolving it in a suitable solvent such as MeOH, EtOH, THF, 1,4-dioxane, water or mixtures thereof and a base like LiOH, NaOH, KOH, $Na_2CO_3$, $K_2CO_3$ or $Cs_2CO_3$. Preferred conditions are NaOH in EtOH/$H_2O$ and LiOH in THF/$H_2O$.

E: Modification of Pyrrolidine Nitrogen

E1: Alkylations

The pyrrolidine nitrogen can be alkylated with an appropriate alyklating agent such as alkyl halides, triflates, mesylates or nosylates in a solvent such as toluene, THF, DMF, $CH_2Cl_2$ or acetonitrile. Furthermore, the nitrogen can be alkylated using aldehydes/ketones and a reducing agent such as $NaCNBH_3$, $NaBH_4$, etc. or formic acid. Elevated temperatures up the boiling point of the respective solvents, multiple additions of alkylating agent and prolonged reaction times up to 10 days might be required in order to drive the reaction to completion.

E2: Acylations and Sulfonylations

The pyrrolidine nitrogen can be acylated or sulfonylated with an appropriate acylating or sulfonylating agent such as acyl halides, acid anhydrides, sulfonyl halides or sulfonyl anhydrides in a solvent such as toluene, THF, DMF, $CH_2Cl_2$ or acetonitrile. Furthermore, the nitrogen can be acylated using an carboxylic acid and an activating agent as described in general procedure B. Elevated temperatures up the boiling point of the respective solvents, multiple additions of acylating/sulfonylating agent and prolonged reaction times up to 6 days might be required in order to drive the reaction to completion.

E3: Urea and Carbamate Formation

The pyrrolidine nitrogen can be treated with appropriate isocyanates to form the corresponding ureas in a solvent such as THF, DMF, $CH_2Cl_2$ or acetonitrile. Furthermore, an activated carbamate can be formed using e.g. 4-nitrophenyl chloro formiate followed by substitution with an appropriate amine at r.t. up to elevated temperatures to build the corresponding ureas. Carbamates can be obtained by reaction of the pyrrolidine nitrogen with alkyl chloroformates, carbonic acid anhydrides or by reaction of an activated carbamate such as (substituted) phenyl carbamates with an appropriate alkoholate.

F: Cyclizations

The compounds, wherein $R^1$ and $R^2$ form $C_{1-6}$ alkylene, $C_{2-7}$ alkenylene or $C_{2-7}$ alkynylene, in which one or two —$CH_2$— may be independently replaced with —O—, —NH—, carbonyl or —$S(O)_n$—, where n is 0, 1 or 2, can be prepared by reaction of the pyrrolidine nitrogen and the adjacent amide group with a bireactive reagent such as 1,2-alkyldihalogenides, haloacidhalogenides, halosufonylhalogenides, diaciddihalogenides, haloakly haloformiate, phosgene and derivatives thereof such as triphosgene, CDI, etc. in the presence of base such as DIEA, TEA, DBU, $Na_2CO_3$, $K_2CO_3$, $Cs_2CO_3$ at temperatures between −10 to 120° C. in an appropriate solvent such as $CH_2Cl_2$, acetonitrile, DMF, DMSO, DMF or THF.

As described above, the compounds of formula (I) are active compounds and inhibit the coagulation factor Xa. These compounds consequently influence both platelet activation which is induced by this factor and plasmatic blood coagulation. They therefore inhibit the formation of thrombi and can be used for the treatment and/or prevention of thrombotic disorders, such as, amongst others, arterial and venous thrombosis, deep vein thrombosis, peripheral arterial occlusive disease (PAOD), unstable angina pectoris, myocardial infarction, coronary artery disease, pulmonary embolism, stroke (cerebral thrombosis) due to atrial fibrillation, inflammation and arteriosclerosis. The compounds of the present invention can also be used in the treatment of acute vessel closure associated with thrombolytic therapy and restenosis, e.g. after transluminal coronary angioplasty (PTCA) or bypass grafting of the coronary or peripheral arteries and in the maintenance of vascular access patency in long term hemodialysis patients. F.Xa inhibitors of this invention may form part of a combination therapy with an anticoagulant with a different mode of action or with a platelet aggregation inhibitor or with a thrombolytic agent. Furthermore, these compounds have an effect on tumour cells and prevent metastases. They can therefore also be used as antitumour agents.

Prevention and/or treatment of thrombotic disorders, particularly arterial or deep vein thrombosis, is the preferred indication.

The invention therefore also relates to pharmaceutical compositions comprising a compound as defined above and a pharmaceutically acceptable excipient.

The invention likewise embraces compounds as described above for use as therapeutically active substances, especially as therapeutically active substances for the treatment and/or prophylaxis of diseases which are associated with the coagulation factor Xa, particularly as therapeutically active substances for the treatment and/or prophylaxis of thrombotic disorders, arterial thrombosis, venous thrombosis, deep vein thrombosis, peripheral arterial occlusive disease, unstable angina pectoris, myocardial infarction, coronary artery disease, pulmonary embolism, stroke due to atrial fibrillation, inflammation, arteriosclerosis, acute vessel closure associated with thrombolytic therapy or restenosis, and/or tumor.

The invention also relates to the use of compounds as described above for the preparation of medicaments for the therapeutic and/or prophylactic treatment of diseases which are associated with the coagulation factor Xa, particularly for the therapeutic and/or prophylactic treatment of thrombotic disorders, arterial thrombosis, venous thrombosis, deep vein thrombosis, peripheral arterial occlusive disease, unstable angina pectoris, myocardial infarction, coronary artery disease, pulmonary embolism, stroke due to atrial fibrillation, inflammation, arteriosclerosis, acute vessel closure associated with thrombolytic therapy or restenosis, and/or tumour. Such medicaments comprise a compound as described above.

The invention also relates to the process and the intermediates for manufacturing the compounds of formula (I) as well as the process for manufacturing the intermediates.

The activity of the low molecular weight substances can, moreover, be characterized in the "prothrombin time" (PT) clotting test. The substances are prepared as a 10 mM solution in DMSO and thereafter made up to the desired dilution in the same solvent. Thereafter, 0.25 ml of human plasma (obtained from whole blood anticoagulated with $\frac{1}{10}$ volume of 108 mM Na citrate) is placed in the instrument-specific sample container. In each case 5 µl of each dilution of the substance-dilution series is then mixed with the plasma provided. This plasma/inhibitor mixture is incubated at 37° C. for 2 minutes. Thereafter, there are pipetted to the semi-automatic device (ACL, Automated Coagulation Laboratory (Instrument Laboratory)) 50 µl of plasma/inhibitor mixture in the measurement container. The clotting reaction is initiated by the addition of 0.1 ml of Dade® Innovin® (recombinant human tissue factor combined with calcium buffer and synthetic phospholipids, Dade Behring, Inc., Cat. B4212-50). The time up to the fibrin cross-linking is determined photooptically from the ACL. The inhibitor concentration, which brought about a doubling of the PT clotting time, is determined by fitting the data to an exponential regression (XLfit).

The compounds of the present invention can furthermore be characterised by the Activated Partial Thromboplastin time (aPTT). This coagulation test can e.g. be run on the ACL 300 Coagulation System (Instrumentation Laboratory) automatic analyzer. The substances are prepared as a 10 mM solution in DMSO and thereafter made up to the desired dilution in the same solvent. The test is performed with the Dade® Actin® FS Activated PTT reagent (purified soy phosphatides in $1.0 \times 10^{-4}$M ellagic acid, stabilizers and preservative, Dade Behring, Inc., Cat. B4218-100). Thereafter, 0.25 ml aliquots of human plasma (obtained from whole blood anticoagulated with $\frac{1}{10}$ volume of 108 mM Na citrate) are spiked with 5 µl of test compound in at least 6 concentrations. 50 µl plasma at 4° C. containing $\frac{1}{50}$ vol. inhibitor in solvent are incubated with 50 µl Dade® Acting FS Activated PTT reagent in water at 37° C. for 3 min., then 50 µl $CaCl_2.2H_2O$ 25 mM in water at 37° C. are added. The time up to the fibrin cross-linking is determined photooptically from the ACL. The inhibitor concentration, which brings about a doubling of the APTT clotting time, is determined by fitting the data to an exponential regression (XLfit).

The $K_i$ values of the active compounds of the present invention preferably amount to about 0.001 to 50 µM, especially about 0.001 to 1 µM. The PT values preferably amount to about 0.5 to 100 µM, especially to about 0.5 to 10 µM. The aPTT values preferably amount to about 0.5 to 100 µM, especially to about 0.5 to 10 µM.

The compounds of formula (I) and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragees, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula (I).

The following Examples serve to illustrate the present invention in more detail. They are, however, not intended to limit its scope in any manner.

EXAMPLES

Example AA

The inhibition of the coagulation factor Xa by the compounds of the present invention can be demonstrated with the aid of a chromogenic peptide substrate assay as described hereinafter. Factor Xa activity was measured spectrophotometrically in microtiter plates in a final volume of 150 μl using the following conditions: Inhibition of human factor Xa (Enzyme Research Laboratories) was tested at an enzyme concentration of 3 nM using the chromogenic substrate S-2222 (Chromogenix AB, Mölndal, Sweden) at 200 nM. The reaction kinetics of the enzyme and the substrate were linear with both time and the enzyme concentration. The inhibitors were dissolved in DMSO and tested at various concentrations up to 100 μM. The inhibitors were diluted using HNPT buffer consisting of HEPES 100 mM, NaCl 140 mM, PEG 6000 0.1% and Tween 80 0.02%, pH 7.8. The cleavage of S-2222 by human factor Xa was followed at 405 nm for 5 minutes at room temperature. The velocity of the reaction was determined by the autoreader from the slope of the linear regression fit to 7 time points (1 minute). The initial velocity for each inhibitor concentration was determined by the slope of at least 4 time points in the linear phase by a linear regression fit (mOD/min$^2$). Apparent dissociation constants $K_i$ were calculated according to Cheng and Prusoff [Cheng, Y. C.; Prusoff, W. H. Relationship between the inhibition constant ($K_i$) and the concentration of the inhibitor that causes 50 percent inhibition ($IC_{50}$) of an enzyme reaction. Biochem. Pharmacol. 1973, 22, 3099-3108.] based on the $IC_{50}$ and the respective $K_m$, determined previously ($K_i=IC_{50}/(1+S/K_m)$). The $K_m$ for the substrate used was determined under the conditions of the test with at least 5 substrate concentrations ranging from 0.5 to 15 times $K_m$. [Lottenberg R, Hall J A, Blinder M, Binder E P, Jackson C M., The action of thrombin on peptide p-nitroanilide substrates. Substrate selectivity and examination of hydrolysis under different reaction conditions. Biochim Biophys Acta. 1983 Feb. 15; 742(3):539-57]. According to Eadie [Eadie G. S. The inhibition of cholinesterase by physostigmine and prostigmine. J. Biol. Chem. 1942, 146, 85-93.], the $K_m$ for S-2222 amounted to 613 μM.

| Example | $K_i$ [μM] factor Xa |
|---|---|
| Example 2 | 0.023 |
| Example 6 | 0.046 |
| Example 14 | 0.042 |
| Example 21 | 0.065 |

Example 1

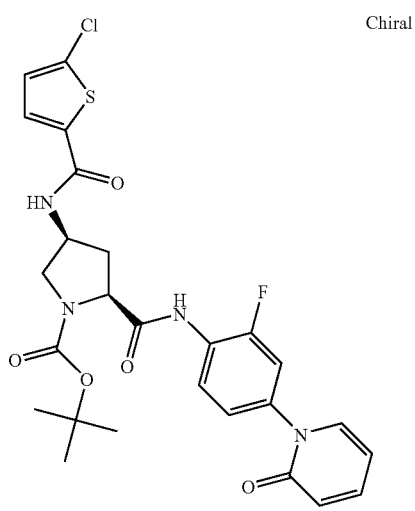

(2S,4S)-4-[(5-Chloro-thiophene-2-carbonyl)-amino]-2-[2-fluoro-4-(2-oxo-2H-pyridin-1-yl)-phenylcarbamoyl]-pyrrolidine-1-carboxylic acid tert-butyl ester 1a) (2S,4S)-4-(9H-Fluoren-9-ylmethoxycarbonylamino)-2-[2-fluoro-4-(2-oxo-2H-pyridin-1-yl)-phenylcarbamoyl]-pyrrolidine-1-carboxylic acid tert-butyl ester:

(2S,4S)-Fmoc-4-Amino-1-Boc-pyrrolidine-2-carboxylic acid (0.5 g) was dissolved under a nitrogen atmosphere in acetonitrile (5 ml). DIEA (280 μl), 1-(4-amino-3-fluoro-phenyl)-1H-pyridin-2-one (248 mg) and BOP-Cl (422 mg) were added stepwise to the solution. The mixture was stirred for 4 d at 25° C. The precipitate was filtered off and the filtrate is evaporated to dryness. The crude product was dissolved in CH$_2$Cl$_2$ (50 ml), washed with 10% aqueous Na$_2$CO$_3$ solution (20 ml) and brine (20 ml). The organic phase was dried over Na$_2$SO$_4$, filtrated and evaporated to dryness. The crude product was purified twice by chromatography (silica gel; gradient: CH$_2$Cl$_2$->methanol and silica gel; gradient n-heptane->AcOEt) to yield (2S,4S)-4-(9H-Fluoren-9-ylmethoxycarbonylamino)-2-[2-fluoro-4-(2-oxo-2H-pyridin-1-yl)-phenylcarbamoyl]-pyrrolidine-1-carboxylic acid tert-butyl ester as a colorless amorphous solid (178 mg). MH$^+$=639.2

1b) (2S,4S)-4-Amino-2-[2-fluoro-4-(2-oxo-2H-pyridin-1-yl)-phenylcarbamoyl]-pyrrolidine-1-carboxylic acid tert-butyl ester (2S,4S)-4-(9H-Fluoren-9-ylmethoxycarbonylamino)-2-[2-fluoro-4-(2-oxo-2H-pyridin-1-yl)-phenylcarbamoyl]-pyrrolidine-1-carboxylic acid tert-butyl ester (160 mg) was dissolved in CH₂Cl₂ (2 ml) and piperidine (43 μl) was added. The mixture was stirred for 17 h at 25° C. The crude product was purified by chromatography (silica gel; gradient: CH₂Cl₂->methanol 2N NH₃) to yield (2S,4S)-4-amino-2-[2-fluoro-4-(2-oxo-2H-pyridin-1-yl)-phenylcarbamoyl]-pyrrolidine-1-carboxylic acid tert-butyl ester as colorless amorphous solid (96 mg). MH⁺=417.5

1c) (2S,4S)-4-[(5-Chloro-thiophene-2-carbonyl)-amino]-2-[2-fluoro-4-(2-oxo-2H-pyridin-1-yl)-phenylcarbamoyl]-pyrrolidine-1-carboxylic acid tert-butyl ester (2S,4S)-4-Amino-2-[2-fluoro-4-(2-oxo-2H-pyridin-1-yl)-phenylcarbamoyl]-pyrrolidine-1-carboxylic acid tert-butyl ester (90 mg) was dissolved in acetonitrile (0.75 ml). A solution of 5-chlorothiophene-2-carboxylic acid (53 mg), NMM (33 mg) and IBCF (44 mg) in acetonitrile (0.75 ml), which was stirred for 30 min at 25° C., was added to the first solution. The complete mixture was stirred for 72 h at 25° C., evaporated to dryness and purified by chromatography (silica gel; gradient: n-heptane->AcOEt) to yield (2S,4S)-4-[(5-chloro-thiophene-2-carbonyl)-amino]2-[2-fluoro-4-(2-oxo-2H-pyridin-1-yl)-phenylcarbamoyl]-pyrrolidine-1-carboxylic acid tert-butyl ester (46 mg) as colorless solid. MH⁺=561.3 (Cl-isotopes)

Example 2

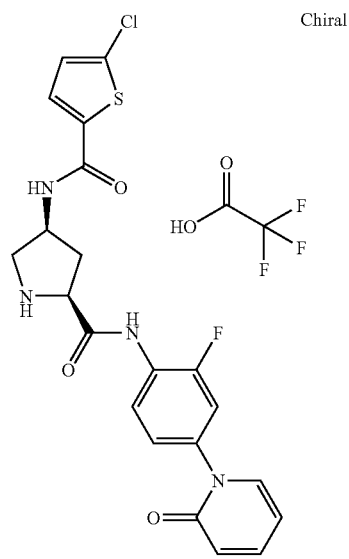

(2S,4S)-4-[(5-Chloro-thiophene-2-carbonyl)-amino]-pyrrolidine-2-carboxylic acid[2-fluoro-4-(2-oxo-2H-pyridin-1-yl)-phenyl]-amide trifluoro-acetate (2S,4S)-4-[(5-Chloro-thiophene-2-carbonyl)-amino]-2-[2-fluoro-4-(2-oxo-2H-pyridin-1-yl)-phenylcarbamoyl]-pyrrolidine-1-carboxylic acid tert-butyl ester (30 mg) was dissolved in CH₂Cl₂ (1 ml) and TFA is added (1 ml). The mixture was stirred for 1 h at 25° C. and evaporated to dryness to yield (2S,4S)-4-[(5-chloro-thiophene-2-carbonyl)-amino]-pyrrolidine-2-carboxylic acid[2-fluoro-4-(2-oxo-2H-pyridin-1-yl)-phenyl]-amide trifluoro-acetate (31 mg) as a colorless solid. MH⁺=461.3 (Cl-isotopes).

Example 3

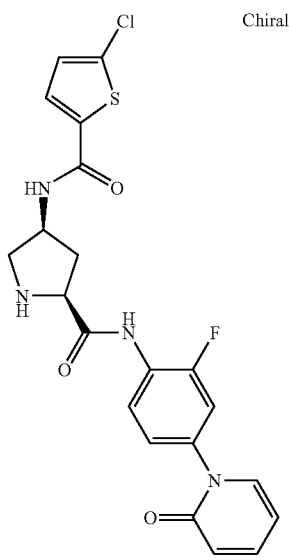

(2S,4S)-4-[(5-Chloro-thiophene-2-carbonyl)-amino]-pyrrolidine-2-carboxylic acid[2-fluoro-4-(2-oxo-2H-pyridin-1-yl)-phenyl]-amide Example 2 was dissolved in CH₂Cl₂ and washed twice with 10% aqueous Na₂CO₃-solution. The aqueous phase was extracted twice with CH₂Cl₂/THF (1:1 v/v) and the organic phases were combined and dried over Na₂SO₄. After filtration the organic phase was evaporated to dryness to yield (2S,4S)-4-[(5-Chloro-thiophene-2-carbonyl)-amino]-pyrrolidine-2-carboxylic acid[2-fluoro-4-(2-oxo-2H-pyridin-1-yl)-phenyl]-amide as a colorless foam (246 mg). MH⁺=461.3 (Cl-isotopes).

Example 4

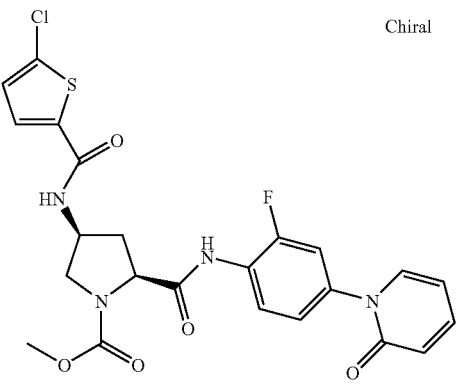

(2S,4S)-4-[(5-Chloro-thiophene-2-carbonyl)-amino]-
2-[2-fluoro-4-(2-oxo-2H-pyridin-1-yl)-phenylcar-
bamoyl]-pyrrolidine-1-carboxylic acid methyl ester Example 3 (105 mg) was dissolved in THF (2 ml) and methyl chloroformiate (40 µl) and DIEA (80 µl) are added. The mixture was stirred for 24 h at 25° C. The mixture was evaporated to dryness and purified by chromatography (silica gel; gradient: $CH_2Cl_2$->methanol 2N $NH_3$) to yield (2S,4S)-4-[(5-chloro-thiophene-2-carbonyl)-amino]-2-[2-fluoro-4-(2-oxo-2H-pyridin-1-yl)-phenylcarbamoyl]-pyrrolidine-1-carboxylic acid methyl ester (84 mg) as a colorless amorphous solid. $MH^+$=519.3 (Cl-isotopes).

Example 5

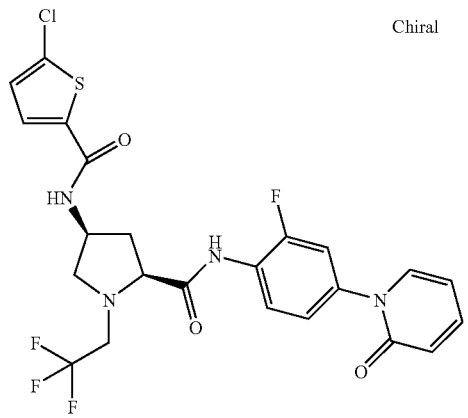

(2S,4S)-4-[(5-Chloro-thiophene-2-carbonyl)-amino]-
1-(2,2,2-trifluoro-ethyl)-pyrrolidine-2-carboxylic
acid[2-fluoro-4-(2-oxo-2H-pyridin-1-yl)-phenyl]-
amide Example 3 (110 mg) was dissolved in THF (2 ml) and 2,2,2-trifluoroethyl triflate (208 mg) and DIEA (150 µl) were added. The mixture was stirred for 24 h at 25° C. To drive the reaction to completion additional 2,2,2-trifluoroethyl triflate (1.5 eq) and DIEA (1.5 eq) were added. The mixture was stirred for 72 h at 25° C. The mixture was evaporated afterwards to dryness and purified by chromatography (silica gel; gradient: $CH_2Cl_2$->methanol 2N $NH_3$) to yield (2S,4S)-4-[(5-chloro-thiophene-2-carbonyl)-amino]-1-(2,2,2-trifluoro-ethyl)-pyrrolidine-2-carboxylic acid[2-fluoro-4-(2-oxo-2H-pyridin-1-yl)-phenyl]-amide (75 mg) as a colorless amorphous solid. $MH^+$=543.2 (Cl-isotopes).

Example 6

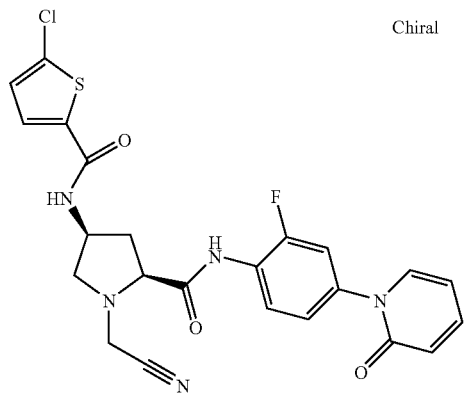

(2S,4S)-4-[(5-Chloro-thiophene-2-carbonyl)-amino]-
1-cyanomethyl-pyrrolidine-2-carboxylic acid[2-
fluoro-4-(2-oxo-2H-pyridin-1-yl)-phenyl]-amide Example 3 (200 mg) was dissolved in acetonitrile (3 ml) and bromoacetonitrile (91 mg) and DIEA (130 µl) are added. The mixture was stirred for 24 h at 25° C. The mixture was evaporated afterwards to dryness and purified by chromatography (silica gel; gradient: n-heptane->AcOEt) to yield (2S,4S)-4-[(5-chloro-thiophene-2-carbonyl)-amino]-1-cyanomethyl-pyrrolidine-2-carboxylic acid[2-fluoro-4-(2-oxo-2H-pyridin-1-yl)-phenyl]-amide (89 mg) as a yellow solid. $MH^+$=500.4 (Cl-isotopes).

Example 7

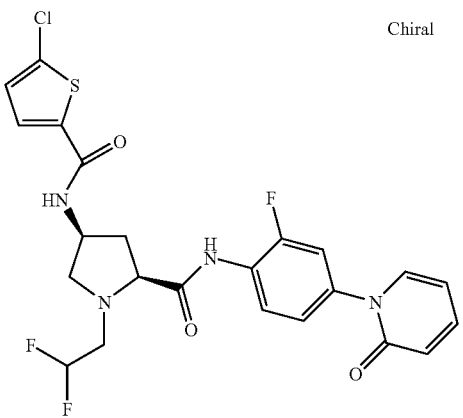

(2S,4S)-4-[(5-Chloro-thiophene-2-carbonyl)-amino]-
1-(2,2-difluoro-ethyl)-pyrrolidine-2-carboxylic acid
[2-fluoro-4-(2-oxo-2H-pyridin-1-yl)-phenyl]-amide Example 7 was prepared in analogy to example 5 to yield (2S,4S)-4-[(5-chloro-thiophene-2-carbonyl)-amino]-1-(2,2-difluoro-ethyl)-pyrrolidine-2-carboxylic acid[2-fluoro-4-(2-oxo-2H-pyridin-1-yl)-phenyl]-amide (64 mg) as a colorless foam. $MH^+$=525.3 (Cl-isotopes).

Example 8

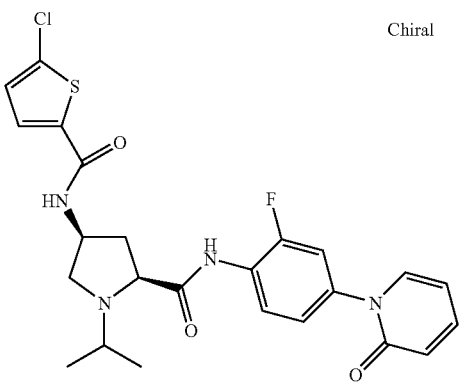

(2S,4S)-4-[(5-Chloro-thiophene-2-carbonyl)-amino]-1-isopropyl-pyrrolidine-2-carboxylic acid [2-fluoro-4-(2-oxo-2H-pyridin-1-yl)-phenyl]-amide Example 3 (150 mg) was suspended in a mixture of methanol/acetic acid 9:1 v/v (1.5 ml) and acetone (265 mg) was added. The mixture was stirred for 30 min at 25° C. Afterwards, sodium cyanoborohydride (143 mg) was added and the mixture was stirred for 72 h at 80° C. The mixture was evaporated to dryness and purified by chromatography (silica gel; gradient: n-heptane->AcOEt) to yield (2S,4S)-4-[(5-chloro-thiophene-2-carbonyl)-amino]-1-isopropyl-pyrrolidine-2-carboxylic acid[2-fluoro-4-(2-oxo-2H-pyridin-1-yl)-phenyl]-amide (40 mg) as a light yellow solid. MH$^+$=503.3 (Cl-isotopes).

Example 9

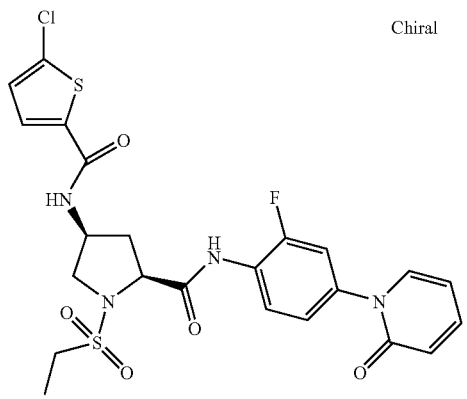

(2S,4S)-4-[(5-Chloro-thiophene-2-carbonyl)-amino]-1-ethanesulfonyl-pyrrolidine-2-carboxylic acid[2-fluoro-4-(2-oxo-2H-pyridin-1-yl)-phenyl]-amide Example 9 was prepared in analogy to example 4 to yield (2S,4S)-4-[(5-chloro-thiophene-2-carbonyl)-amino]-1-ethanesulfonyl-pyrrolidine-2-carboxylic acid[2-fluoro-4-(2-oxo-2H-pyridin-1-yl)-phenyl]-amide (40 mg) as an off-white solid. MH$^+$=553.2 (Cl-isotopes).

Example 10

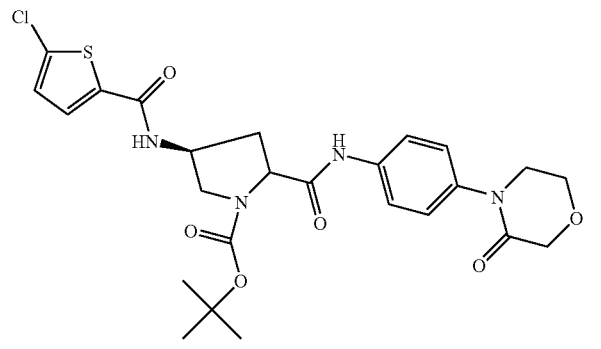

(S)-4-[(5-Chloro-thiophene-2-carbonyl)-amino]-2-[4-(3-oxo-morpholin-4-yl)-phenylcarbamoyl]-pyrrolidine-1-carboxylic acid tert-butyl ester Example 10 was prepared in analogy to example 1, using 4-(4-amino-phenyl)-morpholin-3-one as amine component to yield (S)-4-[(5-chloro-thiophene-2-carbonyl)-amino]-2-[4-(3-oxo-morpholin-4-yl)-phenylcarbamoyl]-pyrrolidine-1-carboxylic acid tert-butyl ester as a white solid (mixture of epimers). MH$^+$=549.1 (Cl-isotopes).

Example 11

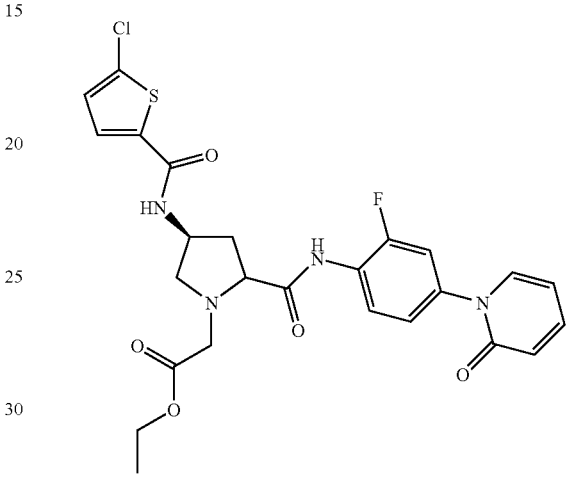

{(S)-4-[(5-Chloro-thiophene-2-carbonyl)-amino]-2-[2-fluoro-4-(2-oxo-2H-pyridin-1-yl)-phenylcarbamoyl]-pyrrolidin-1-yl}-acetic acid ethyl ester Example 11 was prepared from example 3 in analogy to example 6 by, using ethyl bromoacetate to yield {(S)-4-[(5-chloro-thiophene-2-carbonyl)-amino]-2-[2-fluoro-4-(2-oxo-2H-pyridin-1-yl)-phenylcarbamoyl]-pyrrolidin-1-yl}-acetic acid ethyl ester (198 mg) as a mixture of epimers. MH$^+$=547.3 (Cl-isotopes).

Example 12

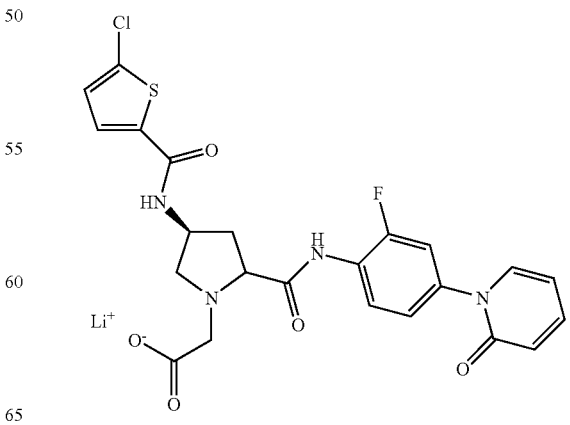

Lithium {(S)-4-[(5-chloro-thiophene-2-carbonyl)-amino]-2-[2-fluoro-4-(2-oxo-2H-pyridin-1-yl)-phenylcarbamoyl]-pyrrolidin-1-yl}-acetate Example 11 (167 mg) was dissolved in THF/water 1:1 v/v (3 ml) and lithium hydroxide mono hydrate (14 mg) was added. The mixture was stirred for 1.5 h at 25° C. and evaporated to dryness to yield lithium {(S)-4-[(5-chloro-thiophene-2-carbonyl)-amino]-2-[2-fluoro-4-(2-oxo-2H-pyridin-1-yl)-phenylcarbamoyl]-pyrrolidin-1-yl}-acetate (168 mg) as an off-white foam. MH$^+$=519.3 (Cl-isotopes).

Example 13

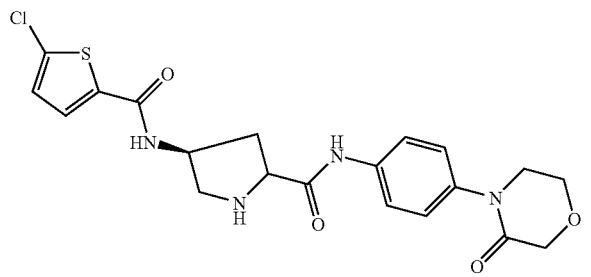

(S)-4-[(5-Chloro-thiophene-2-carbonyl)-amino]-pyrrolidine-2-carboxylic acid[4-(3-oxo-morpholin-4-yl)-phenyl]-amide Example 13 was prepared from example 10 in analogy to examples 2 and 3 to yield (S)-4-[(5-Chloro-thiophene-2-carbonyl)-amino]-pyrrolidine-2-carboxylic acid[4-(3-oxo-morpholin-4-yl)-phenyl]-amide (93 mg) as a light yellow oil (mixture of epimers). MH$^+$=449.3 (Cl-isotopes).

Example 14

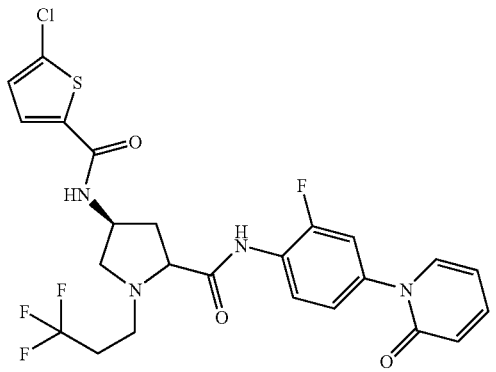

(S)-4-[(5-Chloro-thiophene-2-carbonyl)-amino]-1-(3,3,3-trifluoro-propyl)-pyrrolidine-2-carboxylic acid [2-fluoro-4-(2-oxo-2H-pyridin-1-yl)-phenyl]-amide Example 14 was prepared from example 3 in analogy to example 5, using 1-bromo-3,3,3-trifluoropropane as alkylating agent (15 eq). The mixture is stirred for 72 h at 85° C. and purified as example 5 to yield (S)-4-[(5-chloro-thiophene-2-carbonyl)-amino]-1-(3,3,3-trifluoro-propyl)-pyrrolidine-2-carboxylic acid[2-fluoro-4-(2-oxo-2H-pyridin-1-yl)-phenyl]-amide (69 mg) as a colorless foam (mixture of epimers). MH$^+$=557.3 (Cl-isotopes).

Example 15

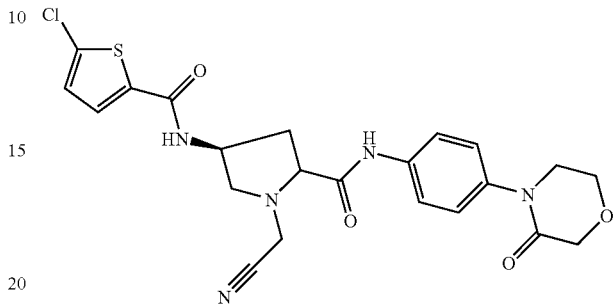

(S)-4-[(5-Chloro-thiophene-2-carbonyl)-amino]-1-cyanomethyl-pyrrolidine-2-carboxylic acid [4-(3-oxo-morpholin-4-yl)-phenyl]-amide Example 15 was prepared from example 13 in analogy to example 6 to yield (S)-4-[(5-chloro-thiophene-2-carbonyl)-amino]-1-cyanomethyl-pyrrolidine-2-carboxylic acid[4-(3-oxo-morpholin-4-yl)-phenyl]-amide (25 mg) as a white solid (mixture of epimers). MH$^+$=557.3 (Cl-isotopes).

Example 16

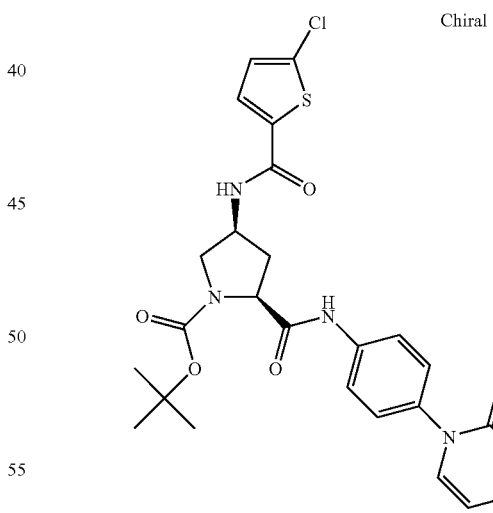

(2S,4S)-4-[(5-Chloro-thiophene-2-carbonyl)-amino]-2-[4-(2-oxo-2H-pyridin-1-yl)-phenylcarbamoyl]-pyrrolidine-1-carboxylic acid tert-butyl ester Example 16 was prepared in analogy to example 1, using 1-(4-amino-phenyl)-1H-pyridin-2-one as amine component to yield (2S,4S)-4-[(5-chloro-thiophene-2-carbonyl)-amino]-2-[4-(2-oxo-2H-pyridin-1-yl)-phenylcarbamoyl]- pyrrolidine-1-carboxylic acid tert-butyl ester as a light brown amorphous solid. MH$^+$=543.1 (Cl-isotopes).

Example 17

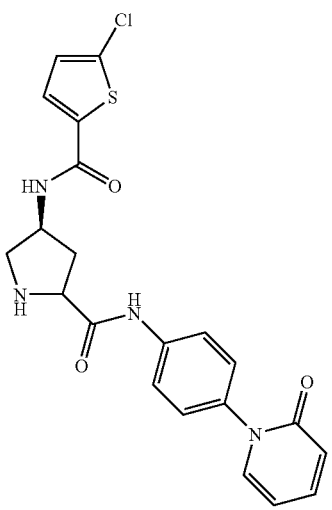

(S)-4-[(5-Chloro-thiophene-2-carbonyl)-amino]-pyrrolidine-2-carboxylic acid[4-(2-oxo-2H-pyridin-1-yl)-phenyl]-amide Example 17 was prepared from example 16 in analogy to examples 2 and 3 to yield (S)-4-[(5-chloro-thiophene-2-carbonyl)-amino]-pyrrolidine-2-carboxylic acid[4-(2-oxo-2H-pyridin-1-yl)-phenyl]-amide as a light brown foam (mixture of epimers). MH$^+$=443.1 (Cl-isotopes).

Example 18

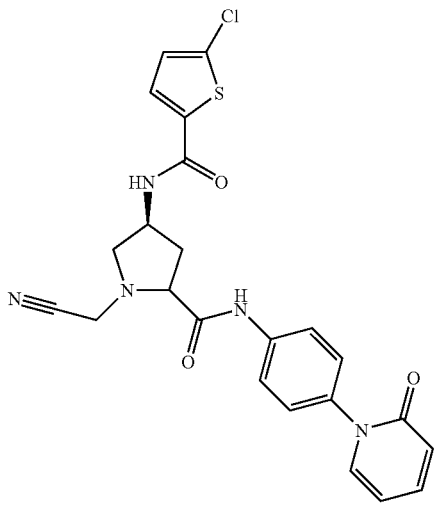

(S)-4-[(5-Chloro-thiophene-2-carbonyl)-amino]-1-cyanomethyl-pyrrolidine-2-carboxylic acid [4-(2-oxo-2H-pyridin-1-yl)-phenyl]-amide Example 18 was prepared from example 17 in analogy to example 6 to yield (S)-4-[(5-chloro-thiophene-2-carbonyl)-amino]-1-cyanomethyl-pyrrolidine-2-carboxylic acid[4-(2-oxo-2H-pyridin-1-yl)-phenyl]-amide as a yellow amorphous solid. MH$^+$=482.3 (Cl-isotopes).

Example 19

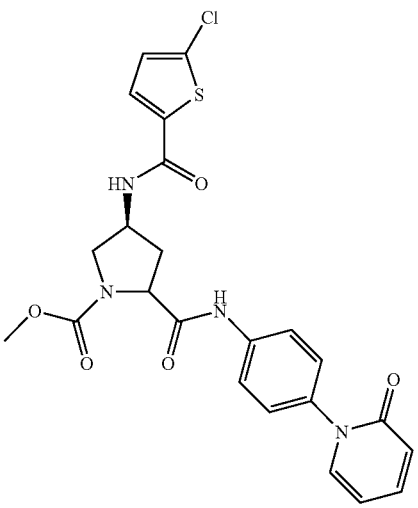

(S)-4-[(5-Chloro-thiophene-2-carbonyl)-amino]-2-[4-(2-oxo-2H-pyridin-1-yl)-phenylcarbamoyl]-pyrrolidine-1-carboxylic acid methyl ester Example 19 was prepared from example 17 in analogy to example 6 to yield (S)-4-[(5-chloro-thiophene-2-carbonyl)-amino]-1-cyanomethyl-pyrrolidine-2-carboxylic acid[4-(2-oxo-2H-pyridin-1-yl)-phenyl]-amide as a yellow amorphous solid. MH$^+$=482.3 (Cl-isotopes).

Example 20

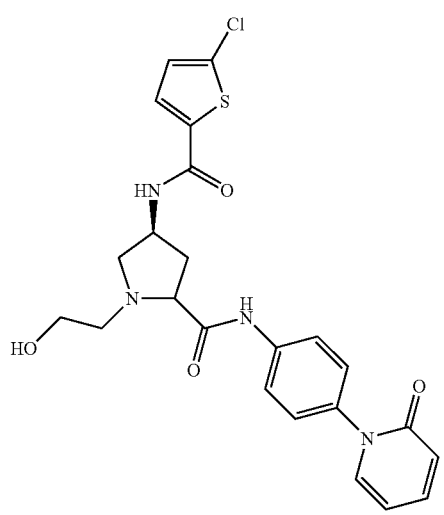

(S)-4-[(5-Chloro-thiophene-2-carbonyl)-amino]-1-(2-hydroxy-ethyl)-pyrrolidine-2-carboxylic acid[4-(2-oxo-2H-pyridin-1-yl)-phenyl]-amide Example 17 (80 mg) was dissolved in acetonitrile (2 ml). DIEA (50 µl) and 2-bromoethanol (40 mg) were added to the solution. The reaction mixture was stirred for 2 days at 85° C. The crude reaction mixture was purified, using preparative HPLC to yield (S)-4-[(5-chloro-thiophene-2-carbonyl)-amino]-1-(2-hydroxy-ethyl)-pyrrolidine-2-carboxylic acid [4-(2-oxo-2H-pyridin-1-yl)-phenyl]-amide (30 mg) as a colorless solid. $MH^+$=487.3 (Cl-isotopes).

Example 21

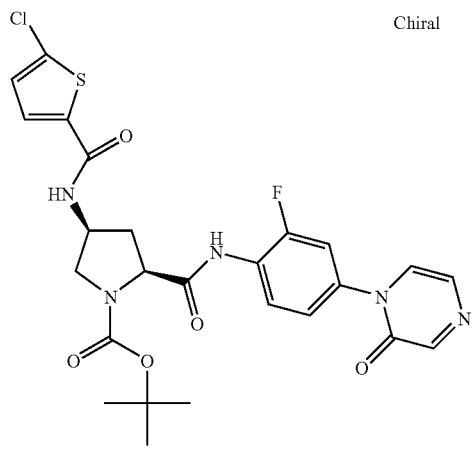

(2S,4S)-4-[(5-Chloro-thiophene-2-carbonyl)-amino]-2-[2-fluoro-4-(2-oxo-2H-pyrazin-1-yl)-phenylcarbamoyl]-pyrrolidine-1-carboxylic acid tert-butyl ester Example 21 was prepared in analogy to example 1, using 1-(4-amino-3-fluoro-phenyl)-1H-pyrazin-2-one as amine component to yield (2S,4S)-4-[(5-Chloro-thiophene-2-carbonyl)-amino]-2-[2-fluoro-4-(2-oxo-2H-pyrazin-1-yl)-phenylcarbamoyl]-pyrrolidine-1-carboxylic acid tert-butyl ester as a colorless foam. $MH^+$=562.5 (Cl-isotopes).

Example 22

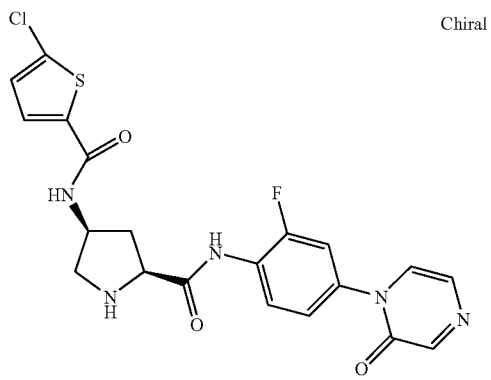

(2S,4S)-4-[(5-Chloro-thiophene-2-carbonyl)-amino]-pyrrolidine-2-carboxylic acid[2-fluoro-4-(2-oxo-2H-pyrazin-1-yl)-phenyl]-amide Example 22 was prepared from example 21 in analogy to examples 2 and 3 to yield (2S,4S)-4-[(5-chloro-thiophene-2-carbonyl)-amino]-pyrrolidine-2-carboxylic acid[2-fluoro-4-(2-oxo-2H-pyrazin-1-yl)-phenyl]-amide as a yellow solid. $MH^+$=462.0 (Cl-isotopes).

Example 23

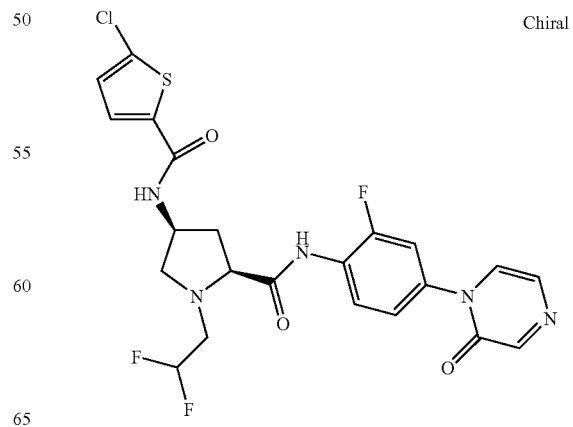

{(2S,4S)-4-[(5-Chloro-thiophene-2-carbonyl)-amino]-2-[2-fluoro-4-(2-oxo-2H-pyrazin-1-yl)-phenylcarbamoyl]-pyrrolidin-1-yl}-acetic acid ethyl ester Example 23 was prepared from example 22 in analogy to example 11 to yield {(2S,4S)-4-[(5-chloro-thiophene-2-carbonyl)-amino]-2-[2-fluoro-4-(2-oxo-2H-pyrazin-1-yl)-phenylcarbamoyl]-pyrrolidin-1-yl}-acetic acid ethyl ester as a yellow amorphous solid. $MH^+$=548.2 (Cl-isotopes).

Example 24

(2S,4S)-4-[(5-Chloro-thiophene-2-carbonyl)-amino]-
1-(2,2-difluoro-ethyl)-pyrrolidine-2-carboxylic acid
[2-fluoro-4-(2-oxo-2H-pyrazin-1-yl)-phenyl]-amide Example 24 was prepared from example 22 in analogy to example 7 to yield (2S,4S)-4-[(5-chloro-thiophene-2-carbonyl)-amino]-1-(2,2-difluoro-ethyl)-pyrrolidine-2-carboxylic acid [2-fluoro-4-(2-oxo-2H-pyrazin-1-yl)-phenyl]-amide as a colorless amorphous solid. $MH^+$=526.3 (Cl-isotopes).

Example 25

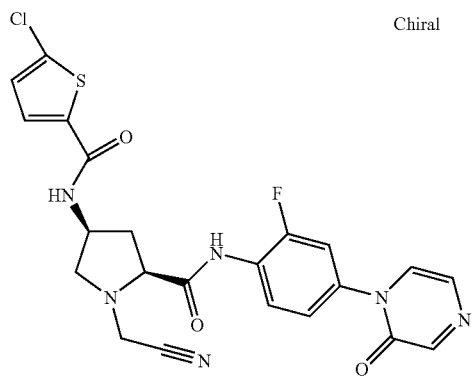

(2S,4S)-4-[(5-Chloro-thiophene-2-carbonyl)-amino]-
1-cyanomethyl-pyrrolidine-2-carboxylic acid[2-
fluoro-4-(2-oxo-2H-pyrazin-1-yl)-phenyl]-amide Example 25 was prepared from example 22 in analogy to example 6 to yield (2S,4S)-4-[(5-chloro-thiophene-2-carbonyl)-amino]-1-cyanomethyl-pyrrolidine-2-carboxylic acid [2-fluoro-4-(2-oxo-2H-pyrazin-1-yl)-phenyl]-amide as a colorless foam. $MH^+$=501.3 (Cl-isotopes).

Example 26

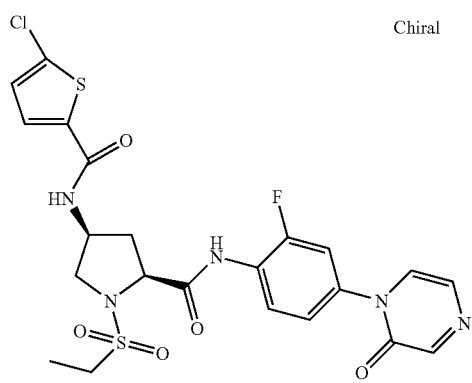

(2S,4S)-4-[(5-Chloro-thiophene-2-carbonyl)-amino]-
1-ethanesulfonyl-pyrrolidine-2-carboxylic acid[2-
fluoro-4-(2-oxo-2H-pyrazin-1-yl)-phenyl]-amide Example 26 was prepared from example 22 in analogy to example 9 to yield (2S,4S)-4-[(5-chloro-thiophene-2-carbonyl)-amino]-1-ethanesulfonyl-pyrrolidine-2-carboxylic acid [2-fluoro-4-(2-oxo-2H-pyrazin-1-yl)-phenyl]-amide as a colorless amorphous foam. $MH^+$=554.3 (Cl-isotopes).

Example 27

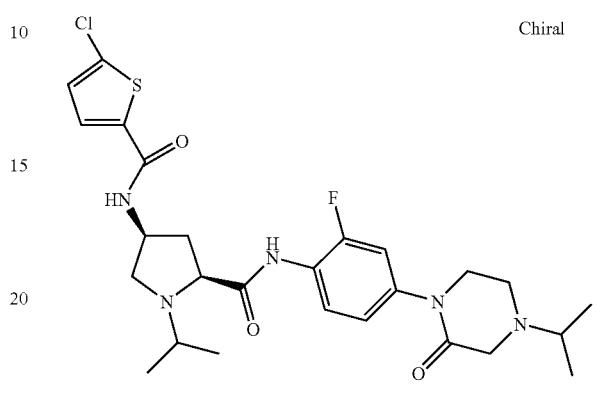

(2S,4S)-4-[(5-Chloro-thiophene-2-carbonyl)-amino]-
1-isopropyl-pyrrolidine-2-carboxylic acid [2-fluoro-
4-(4-isopropyl-2-oxo-piperazin-1-yl)-phenyl]-amide Example 27 was prepared from example 22 in analogy to example 8 to yield (2S,4S)-4-[(5-chloro-thiophene-2-carbonyl)-amino]-1-isopropyl-pyrrolidine-2-carboxylic acid[2-fluoro-4-(4-isopropyl-2-oxo-piperazin-1-yl)-phenyl]-amide as a colorless amorphous foam. $MH^+$=550.3 (Cl-isotopes).

Example 28

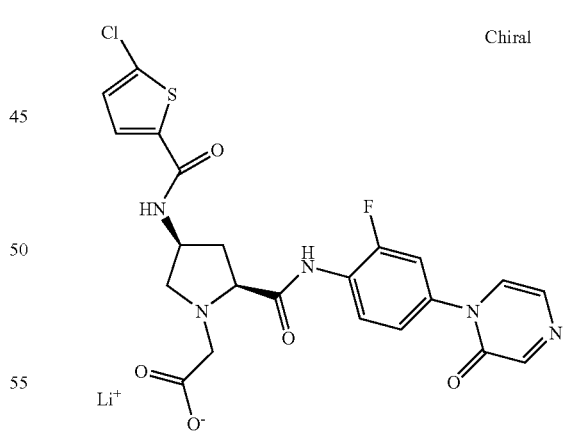

Lithium {(2S,4S)-4-[(5-chloro-thiophene-2-carbonyl)-amino]-2-[2-fluoro-4-(2-oxo-2H-pyrazin-1-yl)-phenylcarbamoyl]-pyrrolidin-1-yl}-acetate Example 28 was prepared from example 23 in analogy to example 12 to yield lithium {(2S,4S)-4-[(5-chloro-thiophene-2-carbonyl)-amino]-2-[2-fluoro-4-(2-oxo-2H- pyrazin-1-yl)-phenylcarbamoyl]-pyrrolidin-1-yl}-acetate as a yellow solid. MH$^+$=520.2 (Cl-isotopes).

Example 29

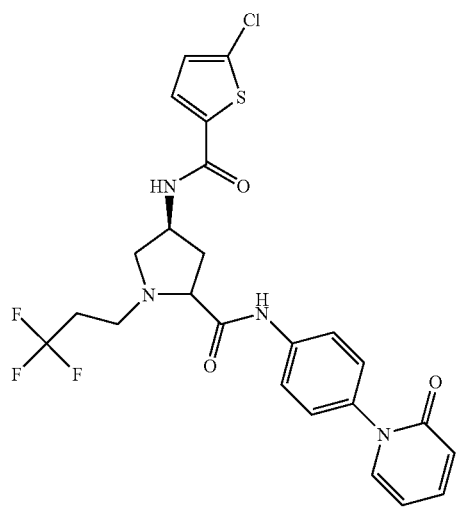

(S)-4-[(5-Chloro-thiophene-2-carbonyl)-amino]-1-(3,3,3-trifluoro-propyl)-pyrrolidine-2-carboxylic acid [4-(2-oxo-2H-pyridin-1-yl)-phenyl]-amide Example 29 was prepared from example 17 in analogy to example 14 after stirring at 85° C. for 10 days to yield (S)-4-[(5-chloro-thiophene-2-carbonyl)-amino]-1-(3,3,3-trifluoro-propyl)-pyrrolidine-2-carboxylic acid[4-(2-oxo-2H-pyridin-1-yl)-phenyl]-amide as a light yellow amorphous solid (mixture of epimers). MH$^+$=539.3 (Cl-isotopes).

Example 30

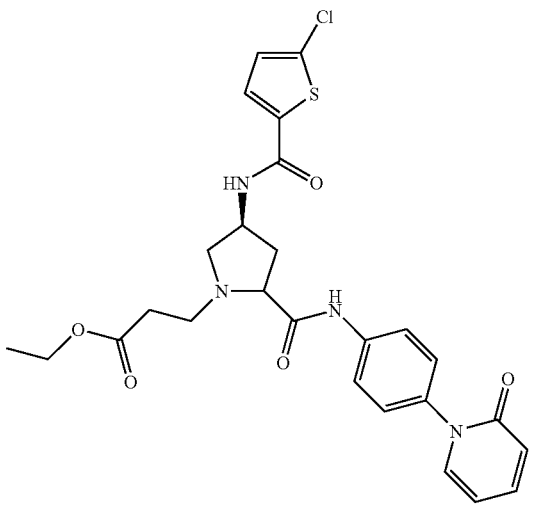

3-{(S)-4-[(5-Chloro-thiophene-2-carbonyl)-amino]-2-[4-(2-oxo-2H-pyridin-1-yl)-phenylcarbamoyl]-pyrrolidin-1-yl}-propionic acid ethyl ester Example 30 was prepared from example 17 in analogy to example 11 after stirring at 75° C. for 2 days to yield 3-{(S)-4-[(5-chloro-thiophene-2-carbonyl)-amino]-2-[4-(2-oxo-2H-pyridin-1-yl)-phenylcarbamoyl]-pyrrolidin-1-yl}-propionic acid ethyl ester as a light yellow amorphous solid (mixture of epimers). MH$^+$=543.3 (Cl-isotopes).

Example 31

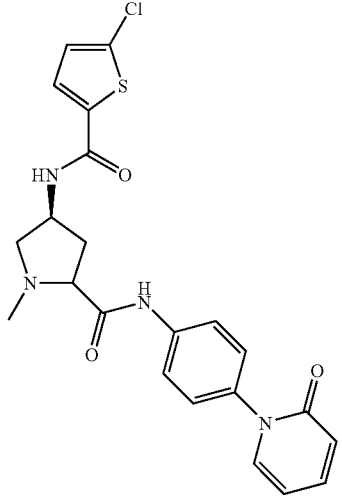

(S)-4-[(5-Chloro-thiophene-2-carbonyl)-amino]-1-methyl-pyrrolidine-2-carboxylic acid[4-(2-oxo-2H-pyridin-1-yl)-phenyl]-amide Example 31 was prepared from example 17, using methyl iodide as alkylating agent in analogy to example 11 after stirring at 25° C. for 2 days to yield (S)-4-[(5-chloro-thiophene-2-carbonyl)-amino]-1-methyl-pyrrolidine-2-carboxylic acid[4-(2-oxo-2H-pyridin-1-yl)-phenyl]-amide as an off-white solid (mixture of epimers). MH$^+$=457.3 (Cl-isotopes).

Example 32

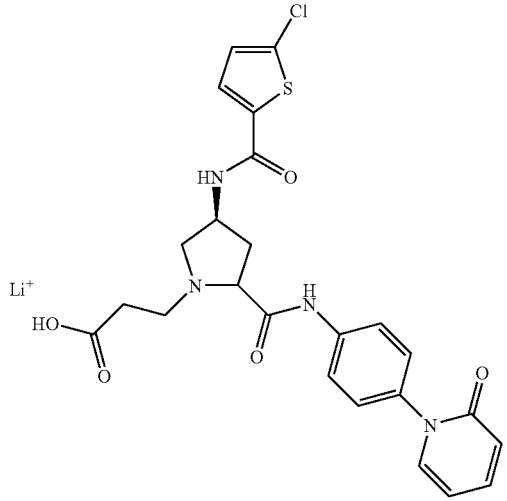

Lithium 3-{(S)-4-[(5-chloro-thiophene-2-carbonyl)-amino]-2-[4-(2-oxo-2H-pyridin-1-yl)-phenylcarbamoyl]-pyrrolidin-1-yl}-propionate Example 32 was prepared from example 30 in analogy to example 12 to yield lithium 3-{(S)-4-[(5-chloro-thiophene-2-carbonyl)-amino]-2-[4-(2-oxo-2H-pyridin-1-yl)-phenylcarbamoyl]-pyrrolidin-1-yl}-propionate as an off-white solid (mixture of epimers). MH+=521.3 (Cl-isotopes).

Example 33

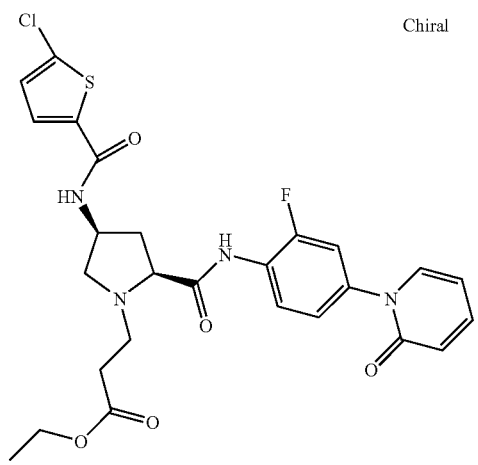

3-{(2S,4S)-4-[(5-Chloro-thiophene-2-carbonyl)-amino]-2-[2-fluoro-4-(2-oxo-2H-pyridin-1-yl)-phenylcarbamoyl]-pyrrolidin-1-yl}-propionic acid ethyl ester Example 33 was prepared from example 3 in analogy to example 30 after stirring at 75° C. for 10 days to yield 3-{(2S,4S)-4-[(5-chloro-thiophene-2-carbonyl)-amino]-2-[2-fluoro-4-(2-oxo-2H-pyridin-1-yl)-phenylcarbamoyl]-pyrrolidin-1-yl}-propionic acid ethyl ester as a light brown amorphous solid. MH+=561.5 (Cl-isotopes).

Example 34

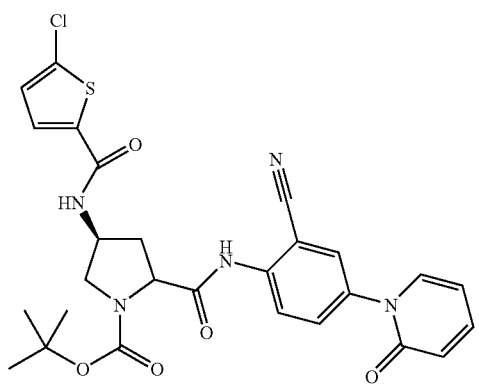

(S)-4-[(5-Chloro-thiophene-2-carbonyl)-amino]-2-[2-cyano-4-(2-oxo-2H-pyridin-1-yl)-phenylcarbamoyl]-pyrrolidine-1-carboxylic acid tert-butyl ester a) (2S,4S)-4-[(5-Chloro-thiophene-2-carbonyl)-amino]-pyrrolidine-1,2-dicarboxylic acid 1-tert-butyl ester 2-methyl ester N-Boc-cis-4-Amino-L-proline methylester hydrochlorid (5 g) was dissolved in acetonitrile (25 ml) and suspended with NMM (1.2 g) for 15 min at 25° C. (Suspension A). 5-Chloro-thiophene-2-carboxylic acid (5.184 g) was dissolved in acetonitrile (25 ml), NMM (2.4 g) and IBCF (4.865 g) were added to the solution. This solution was stirred for 30 min at 25° C. and then added to the above mentioned suspension A. The whole mixture was stirred for 24 h at 25° C. The mixture was then evaporated to dryness and purified by chromatography (silica gel; gradient: $CH_2Cl_2$->methanol 2N $NH_3$) to yield (2S,4S)-4-[(5-chloro-thiophene-2-carbonyl)-amino]-pyrrolidine-1,2-dicarboxylic acid 1-tert-butyl ester 2-methyl ester (5.5 g) as a light yellow gum. MH+=289.1 (Cl-isotopes, loss of Boc-group).

b) 2-Amino-5-(2-oxo-2H-pyridin-1-yl)-benzonitrile

A suspension of 2-amino-5-bromobenzonitrile (1 g), 2-hydroxypyridine (730 mg), CuI (190 mg), potassium carbonate (770 mg) and 8-hydroxyquinoline (150 mg) in 7 ml DMSO was heated for 1.5 h at 160° C. The reaction mixture was afterwards cooled, diluted with $CH_2Cl_2$ and filtered through decalite. The organic phase was extracted with water and brine and purified by chromatography (silica gel, AcOEt/heptane) to yield 2-amino-5-(2-oxo-2H-pyridin-1-yl)-benzonitrile as a yellow solid (120 mg). MH+=212.1 c) (S)-4-[(5-Chloro-thiophene-2-carbonyl)-amino]-2-[2-cyano-4-(2-oxo-2H-pyridin-1-yl)-phenylcarbamoyl]-pyrrolidine-1-carboxylic acid tert-butyl ester (2S,4S)-4-[(5-Chloro-thiophene-2-carbonyl)-amino]-pyrrolidine-1,2-dicarboxylic acid 1-tert-butyl ester 2-methyl ester (example 34a) (75 mg) and 2-amino-5-(2-oxo-2H-pyridin-1-yl)-benzonitrile (example 34b) (49 mg) were suspended in THF (1 ml) under an argon atmosphere and cooled to 0° C. with an ice bath. LiHMDS (460 µl of an 1 M solution in THF) was added drop wise and the mixture is stirred for 30 min at 0° C. and then 2 h at 25° C. After that the mixture was cooled to 0° C. and 2N aqueous HCl solution was added drop wise until pH 1-2 was reached. The product was extracted with AcOEt several times and the combined organic phases were washed with water and brine and dried over $Na_2SO_4$. The organic layer was filtered, evaporated to dryness and the product was purified by chromatography (silica gel; gradient: $CH_2Cl_2$->methanol 2N $NH_3$) to yield (S)-4-[(5-Chloro-thiophene-2-carbonyl)-amino]-2-[2-cyano-4-(2-oxo-2H-pyridin-1-yl)-phenylcarbamoyl]-pyrrolidine-1-carboxylic acid tert-butyl ester (15 mg) as a light brown amorphous solid (mixture of epimers). MH+=468.4 (Cl-isotopes, loss of Boc-group).

Example 35

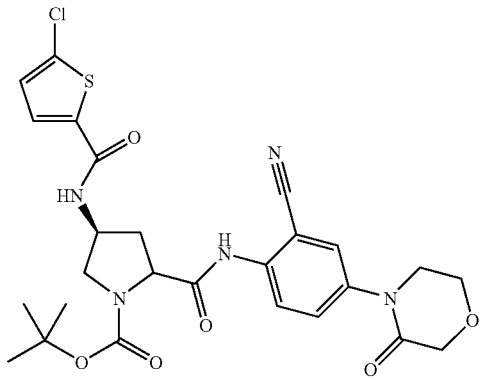

(S)-4-[(5-Chloro-thiophene-2-carbonyl)-amino]-2-[2-cyano-4-(3-oxo-morpholin-4-yl)-phenylcarbamoyl]-pyrrolidine-1-carboxylic acid tert-butyl ester a) 2-Nitro-5-(3-oxo-morpholin-4-yl)-benzonitrile A suspension of 5-chloro-2-nitrobenzonitrile (2.41 g), morpholin-3-one (2 g), cesium carbonate (6.45 g), tris(dibenzylideneacetone)dipalladium (120 mg) and 4,5-bis(diphenylphosphino)-9,9-dimethylxanthene (230 mg) in 30 ml dioxane was heated for 24 h at 120° C. The reaction mixture was cooled to 25° C., diluted with CH$_2$Cl$_2$ and filtered through decalite. The organic layer was washed with water and brine and purified by chromatography (silica gel, AcOEt) to yield 2-nitro-5-(3-oxo-morpholin-4-yl)-benzonitrile as a yellow solid (1.77 g). MH+=248.3 b) 2-Amino-5-(3-oxo-morpholin-4-yl)-benzonitrile

2-Nitro-5-(3-oxo-morpholin-4-yl)-benzonitrile (1.1 g) was dissolved in THF (80 ml) and hydrogenated with hydrogen (1 atm) over Pd/C 10% (350 mg) for 18 h at 25° C. The reaction mixture was then filtered through decalite and precipitated (AcOEt/heptane) to yield 2-amino-5-(3-oxo-morpholin-4-yl)-benzonitrile as a white solid (580 mg). MH+=218.4 c) (S)-4-[(5-Chloro-thiophene-2-carbonyl)-amino]-2-[2-cyano-4-(3-oxo-morpholin-4-yl)-phenylcarbamoyl]-pyrrolidine-1-carboxylic acid tert-butyl ester The title compound was synthesized in analogy to example 34c) to yield (S)-4-[(5-chloro-thiophene-2-carbonyl)-amino]-2-[2-cyano-4-(3-oxo-morpholin-4-yl)-phenylcarbamoyl]-pyrrolidine-1-carboxylic acid tert-butyl ester (11 mg) as a light brown amorphous solid (mixture of epimers). MH+=474.1 (Cl-isotopes, loss of Boc-group).

Example 36

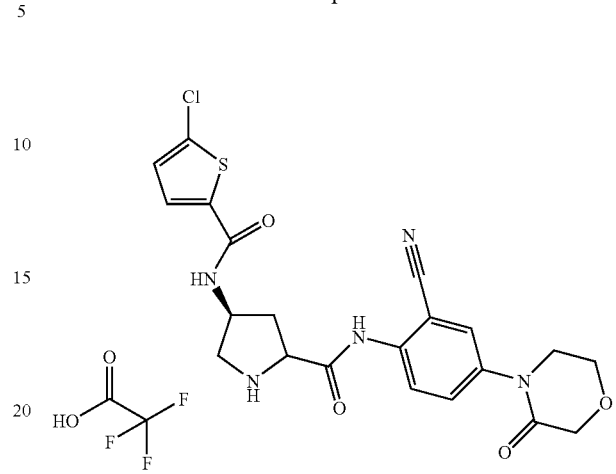

(S)-4-[(5-Chloro-thiophene-2-carbonyl)-amino]-pyrrolidine-2-carboxylic acid[2-cyano-4-(3-oxo-morpholin-4-yl)-phenyl]-amide trifluoro-acetate Example 36 was prepared from example 35 in analogy to example 2 to yield (S)-4-[(5-Chloro-thiophene-2-carbonyl)-amino]-pyrrolidine-2-carboxylic acid[2-cyano-4-(3-oxo-morpholin-4-yl)-phenyl]-amide trifluoro-acetate as brown gum. MH+=474.1 (Cl-isotopes).

Example 37

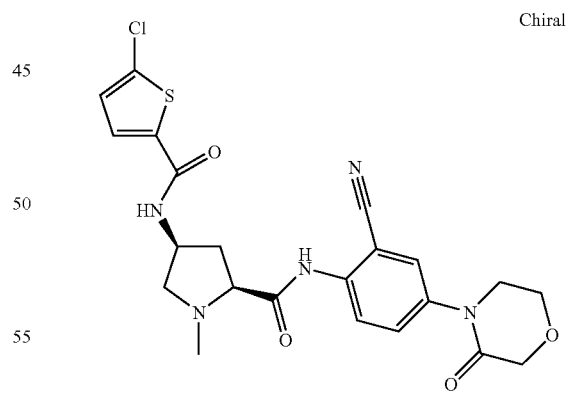

(2S,4S)-4-[(5-Chloro-thiophene-2-carbonyl)-amino]-1-methyl-pyrrolidine-2-carboxylic acid[2-cyano-4-(3-oxo-morpholin-4-yl)-phenyl]-amide Example 37 was prepared from example 36 in analogy to example 31 to yield (2S,4S)-4-[(5-Chloro-thiophene-2-carbonyl)-amino]-1-methyl-pyrrolidine-2-carboxylic acid[2- cyano-4-(3-oxo-morpholin-4-yl)-phenyl]-amide as colorless amorphous solid. MH+=488.1 (Cl-isotopes).

Example 38

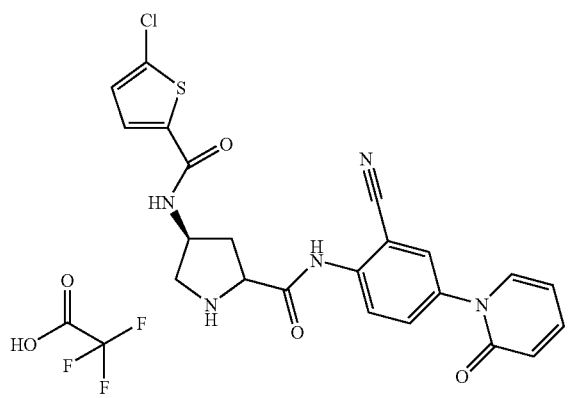

(S)-4-[(5-Chloro-thiophene-2-carbonyl)-amino]-pyrrolidine-2-carboxylic acid[2-cyano-4-(2-oxo-2H-pyridin-1-yl)-phenyl]-amide trifluoro-acetate Example 38 was prepared from example 34 in analogy to example 2 to yield (S)-4-[(5-Chloro-thiophene-2-carbonyl)-amino]-pyrrolidine-2-carboxylic acid[2-cyano-4-(2-oxo-2H-pyridin-1-yl)-phenyl]-amide trifluoro-acetate as a brown foam. MH+=468.4 (Cl-isotopes).

Example 39

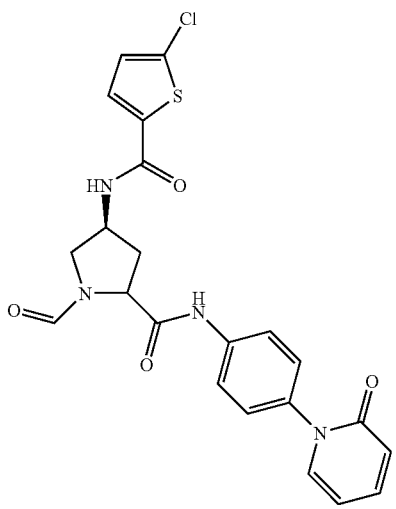

(S)-4-[(5-Chloro-thiophene-2-carbonyl)-amino]-1-formyl-pyrrolidine-2-carboxylic acid[4-(2-oxo-2H-pyridin-1-yl)-phenyl]-amide Example 17 (100 mg) was dissolved in acetonitrile (2 ml) and formic acid 4-nitro-phenyl ester (42 mg) is added. The mixture is stirred for 3 days at 25° C. The mixture is evaporated to dryness, the remaining material dissolved in CH2Cl2/ THF (1:1 v/v; 5 ml) and the organic layer washed with 10% aqueous Na2CO3 solution. The organic layer is dried over Na2SO4, filtered, evaporated to dryness and purified with preparative HPLC to yield (S)-4-[(5-Chloro-thiophene-2-carbonyl)-amino]-1-formyl-pyrrolidine-2-carboxylic acid[4-(2-oxo-2H-pyridin-1-yl)-phenyl]-amide as a light yellow solid (mixture of epimers). MH+=471.3 (Cl-isotopes).

Example 40

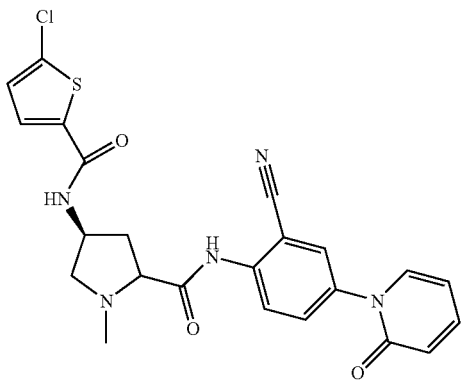

(S)-4-[(5-Chloro-thiophene-2-carbonyl)-amino]-1-methyl-pyrrolidine-2-carboxylic acid[2-cyano-4-(2-oxo-2H-pyridin-1-yl)-phenyl]-amide Example 40 was prepared from example 38 in analogy to example 37 to yield (S)-4-[(5-Chloro-thiophene-2-carbonyl)-amino]-1-methyl-pyrrolidine-2-carboxylic acid[2-cyano-4-(2-oxo-2H-pyridin-1-yl)-phenyl]-amide as light yellow solid. MH+=482.1 (Cl-isotopes).

Example 41

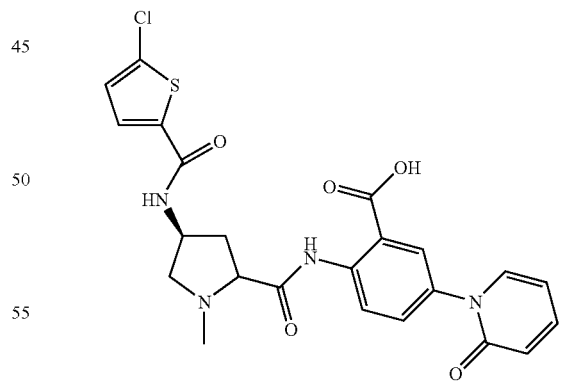

2-({(S)-4-[(5-Chloro-thiophene-2-carbonyl)-amino]-1-methyl-pyrrolidine-2-carbonyl}-amino)-5-(2-oxo-2H-pyridin-1-yl)-benzoic acid Example 41 was isolated as a by-product obtained during hydrolysis of the nitrile group of example 40 to yield 2-({(S)-4-[(5-chloro-thiophene-2-carbonyl)-amino]-1-methyl-pyrrolidine-2-carbonyl}-amino)-5-(2-oxo-2H-pyridin-1-yl)-benzoic acid as white solid. MH$^+$=501.1 (Cl-isotopes).

Example 42

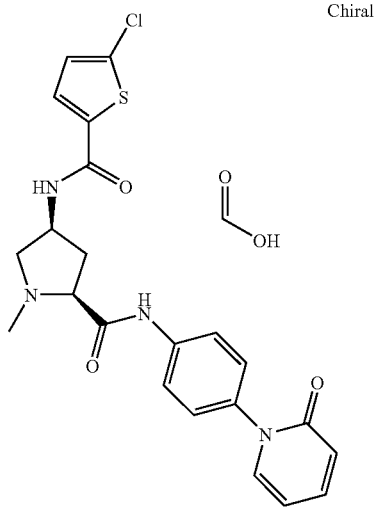

(2S,4S)-4-[(5-Chloro-thiophene-2-carbonyl)-amino]-1-methyl-pyrrolidine-2-carboxylic acid[4-(2-oxo-2H-pyridin-1-yl)-phenyl]-amide formiate Example 42 was isolated after purification of the epimeric mixture of example 31 with preparative HPLC as single enantiomer to yield (2S,4S)-4-[(5-chloro-thiophene-2-carbonyl)-amino]-1-methyl-pyrrolidine-2-carboxylic acid[4-(2-oxo-2H-pyridin-1-yl)-phenyl]-amide formiate as an off-white solid. MH$^+$=457.3 (Cl-isotopes)

Example 43

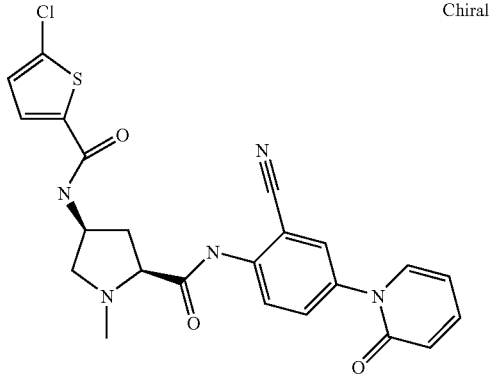

(2S,4S)-4-[(5-Chloro-thiophene-2-carbonyl)-amino]-1-methyl-pyrrolidine-2-carboxylic acid[2-cyano-4-(2-oxo-2H-pyridin-1-yl)-phenyl]-amide Example 43 was isolated after purification of the epimeric mixture of example 40 with preparative HPLC as single enantiomer to yield (2S,4S)-4-[(5-chloro-thiophene-2-carbonyl)-amino]-1-methyl-pyrrolidine-2-carboxylic acid[2-cyano-4-(2-oxo-2H-pyridin-1-yl)-phenyl]-amide as a colorless solid. MH$^+$=482.1 (Cl-isotopes).

Example 44

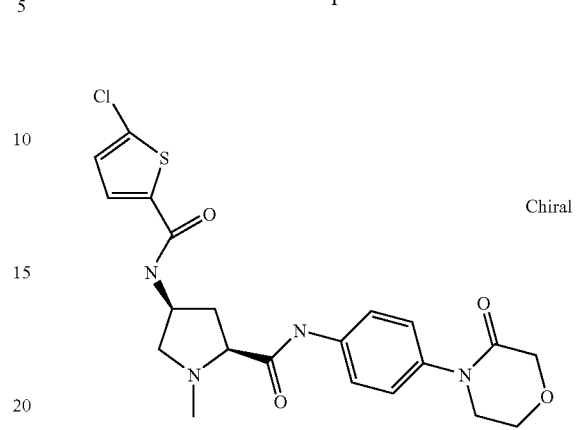

(2S,4S)-4-[(5-Chloro-thiophene-2-carbonyl)-amino]-1-methyl-pyrrolidine-2-carboxylic acid[4-(3-oxo-morpholin-4-yl)-phenyl]-amide Example 44 was prepared from example 13 in analogy to example 31 to yield (2S,4S)-4-[(5-chloro-thiophene-2-carbonyl)-amino]-1-methyl-pyrrolidine-2-carboxylic acid[4-(3-oxo-morpholin-4-yl)-phenyl]-amide as a light yellow solid. MH$^+$=463.3 (Cl-isotopes).

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| Compound of formula (I) | 3.0 mg |
|---|---|
| Polyethylene Glycol 400 | 150.0 mg |
| Acetic Acid | q.s. ad pH 5.0 |
| Water for injection solutions | Ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| Compound of formula (I) | 50.0 mg |
|---|---|
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

What is claimed is:

1. A compound of formula (I):

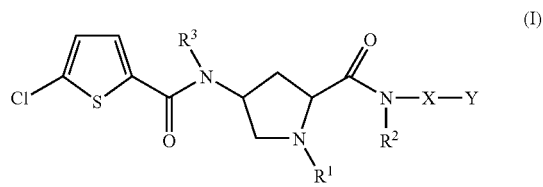

or a pharmaceutically acceptable salt thereof, wherein:

$R^1$ is selected from the group consisting of: (1) hydrogen, (2) optionally substituted $C_{1-6}$-alkyl, (3) optionally substituted $C_{3-7}$-cycloalkyl, (4) optionally substituted $C_{3-7}$-cycloalkyl-$C_{1-6}$-alkyl, (5) optionally substituted $C_{2-6}$-alkenyl, (6) optionally substituted $C_{2-6}$-alkynyl, (7) $R^4C(O)$—, (8) $R^4OC(O)$—, (9) $N(R^5,R^6)C(O)$—, (10) $R^4OC(O)$—$C_{1-6}$-alkyl, (11) $N(R^5,R^6)C(O)$—$C_{1-6}$-alkyl, (12) $R^4$—$SO_2$—, (13) $R^4$—$SO_2$—$C_{1-6}$-alkyl, (14) $N(R^5,R^6)$—$SO_2$—, (15) $N(R^5,R^6)$—$SO_2$—$C_{1-6}$-alkyl, (16) heteroaryl, (17) heteroaryl-$C_{1-6}$-alkyl, (18) aryl, and (19) aryl-$C_{1-6}$-alkyl;

$R^2$ is hydrogen or $C_{1-6}$ alkyl; or $R^1$ and $R^2$ form $C_{1-6}$ alkylene, $C_{2-7}$ alkenylene or $C_{2-7}$ alkynylene, wherein one or two —$CH_2$— groups may be independently replaced with —O—, —NH—, carbonyl or —$S(O)_n$—, where n is 0, 1 or 2;

$R^3$ is hydrogen or $C_{1-6}$ alkyl;

$R^4$ is hydrogen, optionally substituted $C_{1-6}$-alkyl, optionally substituted $C_{3-7}$ cycloalkyl, optionally substituted $C_{3-7}$ cycloalkyl-$C_{1-6}$-alkyl, aryl, aryl-$C_{1-6}$-alkyl, heteroaryl or heteroaryl-$C_{1-6}$-alkyl;

$R^5$ and $R^6$ independently from each other are selected from the group consisting of: (1) hydrogen, (2) optionally substituted $C_{1-6}$-alkyl, (3) optionally substituted $C_{3-7}$ cycloalkyl, (4) optionally substituted $C_{3-7}$ cycloalkyl-$C_{1-6}$-alkyl, (5) aryl, (6) aryl-$C_{1-6}$-alkyl, (7) heteroaryl and (8) heteroaryl-$C_{1-6}$-alkyl; or $R^5$ and $R^6$, together with the nitrogen atom to which they are attached, form a heterocyclic ring selected from the group consisting of piperidinyl, piperazinyl, morpholinyl, pyrrolidinyl, pyrrolinyl and azetidinyl, said heterocyclic ring being optionally substituted by one or more substituents independently selected from the group consisting of $C_{1-6}$-alkyl, halogen and hydroxy;

X is arylene, heteroarylene or heterocyclylene, said arylene, heteroarylene or heterocyclylene being optionally substituted by one or more substituents independently selected from the group consisting of : (1) $C_{1-6}$ alkyl, (2) $C_{3-7}$ cycloalkyl, (3) $C_{3-7}$ cycloalkyl-$C_{1-6}$-alkyl, (4) $C_{1-6}$ alkoxy, (5) fluoro-$C_{1-6}$ alkoxy, (6) carboxyl, (7) halogen, (8) cyano, (9) nitro, (10) amino, (11) —N(R')—CO—($C_{1-6}$ alkyl optionally substituted by one or more fluorine atoms), wherein R' is hydrogen, $C_{1-6}$ alkyl or fluoro $C_{1-6}$ alkyl, (12) —N(R')—CO—O—($C_{1-6}$ alkyl optionally substituted by one or more fluorine atoms), wherein R' is hydrogen, $C_{1-6}$ alkyl or fluoro $C_{1-6}$ alkyl, (13) —N(R')—CO—N(R'') (R'''), wherein R', R'' and R''' are independently hydrogen, $C_{1-6}$ alkyl or fluoro $C_{1-6}$ alkyl, (14) —C(O)—N(R')(R''), wherein R' and R'' are independently hydrogen, $C_{1-6}$ alkyl or fluoro $C_{1-6}$ alkyl, or R' and R'', together with the nitrogen atom to which they are attached, form heterocycyl, (15) —NR'R'', wherein R' and R'' are independently hydrogen, $C_{1-6}$ alkyl or fluoro $C_{1-6}$ alkyl, or R' and R'', together with the nitrogen atom to which they are attached, form heterocycyl, (16)

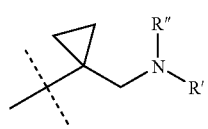

wherein R' and R'' are independently $C_{1-6}$ alkyl or fluoro $C_{1-6}$ alkyl, or R' and R'', together with the nitrogen atom to which they are attached, form heterocyclyl, (17)

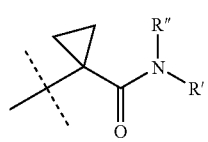

wherein R' and R'' are independently $C_{1-6}$ alkyl or fluoro $C_{1-6}$ alkyl, or R' and R'', together with the nitrogen atom to which they are attached, form heterocyclyl, (18)

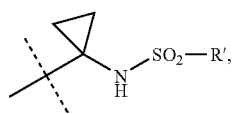

wherein R' is fluoro $C_{1-6}$ alkyl and (19)

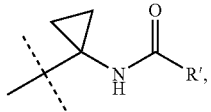

wherein R' is fluoro $C_{1-6}$ alkyl, wherein one or two carbon atoms of said arylene, heteroarylene or heterocyclylene are optionally replaced with a carbonyl group;

Y is hydrogen, aryl, heteroaryl or heterocyclyl, said aryl, heteroaryl or heterocyclyl being optionally substituted by one or more substituents independently selected from the group consisting of: (1) $C_{1-6}$ alkyl optionally substituted by one or more fluorine atoms, (2) $C_{1-6}$ alkoxy optionally substituted by one or more fluorine atoms, (3) halogen, (4) cyano, (5) nitro, (6) amino, (7) mono- or di-$C_{1-6}$ alkyl substituted amino, wherein said $C_{1-6}$ alkyl is optionally substituted by one or more fluorine atoms, (8) mono- or di-$C_{1-6}$ alkyl substituted amino-$C_{1-6}$ alkyl, wherein said $C_{1-6}$ alkyl is optionally substituted by one or more fluorine atoms, (9) —SO$_2$—$C_{1-6}$ alkyl, wherein said $C_{1-6}$ alkyl is optionally substituted by one or more fluorine atoms, (10) —SO$_2$—NH$_2$, (11) —SO$_2$—NH—$C_{1-6}$ alkyl, wherein said $C_{1-6}$ alkyl is optionally substituted by one or more fluorine atoms, and (12) —SO$_2$—N($C_{1-6}$ alkyl)$_2$, wherein said $C_{1-6}$ alkyl is optionally substituted by one or more fluorine atoms, and wherein one or two carbon atoms of said aryl, heteroaryl or heterocyclyl are optionally replaced with a carbonyl group.

2. A compound according to claim 1, wherein X is arylene, heteroarylene or heterocyclylene, said arylene, heteroarylene or heterocyclylene being optionally substituted by one or more substituents independently selected from the group consisting of: (1) $C_{1-6}$ alkyl, (2) $C_{3-7}$ cycloalkyl, (3) $C_{3-7}$ cycloalkyl-$C_{1-6}$-alkyl, (4) $C_{1-6}$ alkoxy, (5) fluoro-$C_{1-6}$ alkoxy, (6) halogen, (7) cyano, (8) nitro, (9) amino, (10) —N(R')—CO—($C_{1-6}$ alkyl optionally substituted by one or more fluorine atoms), wherein R' is hydrogen, $C_{1-6}$ alkyl or fluoro $C_{1-6}$ alkyl, (11) —N(R')—CO—O—($C_{1-6}$ alkyl optionally substituted by one or more fluorine atoms), wherein R' is hydrogen, $C_{1-6}$ alkyl or fluoro $C_{1-6}$ alkyl, (12) —N(R')—CO—N(R'') (R'''), wherein R', R'' and R''' are independently hydrogen, $C_{1-6}$ alkyl or fluoro $C_{1-6}$ alkyl, (13) —C(O)—N(R')(R''), wherein R' and R'' are independently hydrogen, $C_{1-6}$ alkyl or fluoro $C_{1-6}$ alkyl, or R' and R'', together with the nitrogen atom to which they are attached, form heterocycyl, (14) —NR'R'', wherein R' and R'' are independently hydrogen, $C_{1-6}$ alkyl or fluoro $C_{1-6}$ alkyl, or R' and R'', together with the nitrogen atom to which they are attached, form heterocycyl, (15)

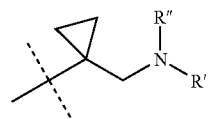

wherein R' and R'' are independently $C_{1-6}$ alkyl or fluoro $C_{1-6}$ alkyl, or R' and R'', together with the nitrogen atom to which they are attached, form heterocyclyl, (16)

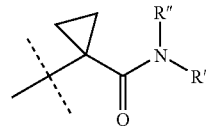

wherein R' and R'' are independently $C_{1-6}$ alkyl or fluoro $C_{1-6}$ alkyl, or R' and R'', together with the nitrogen atom to which they are attached, form heterocyclyl, (17)

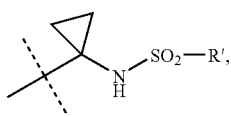

wherein R' is fluoro $C_{1-6}$ alkyl and (18)

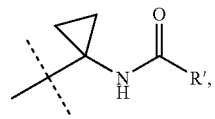

wherein R' is fluoro C$_{1-6}$ alkyl, wherein one or two carbon atoms of said arylene, heteroarylene or heterocyclylene are optionally replaced with a carbonyl group.

3. A compound according to claim 2, wherein:

X is phenylene, optionally substituted by one or more substituents independently selected from the group consisting of halogen and cyano; and Y is heteroaryl or heterocyclyl, wherein said heteroaryl or heterocyclyl are optionally substituted by one or more of the same or different C$_{1-6}$ alkyl groups, and wherein one or two carbon atoms of said heteroaryl or heterocyclyl are optionally replaced with a carbonyl group.

4. A compound according to claim 3, wherein X is 1,4-phenylene optionally substituted by one substituent selected from the group consisting of fluorine and cyano.

5. A compound according to claim 4, wherein X is 1,4-phenylene, 2-fluoro-1,4-phenylene or 2-cyano-1,4-phenylene.

6. A compound according to claim 1, wherein Y is heteroaryl or heterocyclyl, said heteroaryl or heterocyclyl being a mono-cyclic radical of six ring atoms wherein one or two ring atoms are heteroatoms selected from N and O, the remaining ring atoms being C, wherein one carbon atom of said heteroaryl or heterocyclyl is optionally replaced with a carbonyl group.

7. A compound according to claim 6, wherein Y is pyridyl, pyrazinyl or morpholinyl, wherein one carbon atom of said pyridyl, pyrazinyl or morpholinyl is replaced with a carbonyl group.

8. A compound of claim 6, wherein Y is 2-oxo-1-pyridyl, 2-oxo-1-pyrazinyl or 3-oxo-4-morpholinyl.

9. A compound according to claim 1, wherein R$^1$ is hydrogen, optionally substituted C$_{1-6}$-alkyl, R$^4$C(O)—, R$^4$OC(O)—, R$^4$OC(O)—C$_{1-6}$-alkyl, N(R$^5$,R$^6$)C(O)—, N(R$^5$,R$^6$)C(O)—C$_{1-6}$-alkyl, R$^4$—SO$_2$— or R$^4$—SO$_2$—C$_{1-6}$-alkyl, wherein R$^4$ is hydrogen or optionally substituted C$_{1-6}$-alkyl.

10. A compound according to claim 9, wherein R$^1$ is hydrogen, optionally substituted C$_{1-6}$-alkyl, R$^4$OC(O)— or R$^4$OC(O)—C$_{1-6}$-alkyl, wherein R$^4$ is C$_{1-6}$-alkyl.

11. A compound according to claim 10, wherein R$^1$ is hydrogen or C$_{1-6}$-alkyl.

12. A compound according to claim 11, wherein R$^2$ is hydrogen or C$_{1-6}$ alkyl.

13. A compound according to claim 12, wherein R$^2$ is hydrogen.

14. A compound according to claim 1, wherein R$^1$ and R$^2$ form C$_{1-6}$ alkylene, C$_{2-7}$ alkenylene or C$_{2-7}$ alkynylene, wherein one or two —CH$_2$— groups may be independently replaced with —O—, —NH—, carbonyl or —S(O)$_n$—, where n is 0, 1 or 2.

15. A compound according to claim 1, wherein R$^3$ is hydrogen.

16. A compound according to claim 1, selected from the group consisting of:

(2S,4S)-4-[(5-Chloro-thiophene-2-carbonyl)-amino]-pyrrolidine-2-carboxylic acid[2-fluoro-4-(2-oxo-2H-pyridin-1-yl)-phenyl]-amide trifluoro-acetate, (2S,4S)-4-[(5-Chloro-thiophene-2-carbonyl)-amino]-pyrrolidine-2-carboxylic acid[2-fluoro-4-(2-oxo-2H-pyridin-1-yl)-phenyl]-amide, (S)-4-[(5-Chloro-thiophene-2-carbonyl)-amino]-pyrrolidine-2-carboxylic acid[4-(2-oxo-2H-pyridin-1-yl)-phenyl]-amide, (S)-4-[(5-Chloro-thiophene-2-carbonyl)-amino]-1-(2-hydroxy-ethyl)-pyrrolidine-2-carboxylic acid[4-(2-oxo-2H-pyridin-1-yl)-phenyl]-amide, (2S,4S)-4-[(5-Chloro-thiophene-2-carbonyl )-amino]-pyrrolidine-2-carboxylic acid[2-fluoro-4-(2-oxo-2H-pyrazin-1-yl)-phenyl]-amide, (S)-4-[(5-Chloro-thiophene-2-carbonyl)-amino]-1-methyl-pyrrolidine-2-carboxylic acid [4-(2-oxo-2H-pyridin-1-yl)-phenyl]-amide, 3-{(2S,4S)-4-[(5-Chloro-thiophene-2-carbonyl)-amino]-2-[2-fluoro-4-(2-oxo-2H-pyridin-1-yl)-phenylcarbamoyl]-pyrrolidin-1-yl}-propionic acid ethyl ester, (S)-4-[(5-Chloro-thiophene-2-carbonyl)-amino]-2-[2-cyano-4-(2-oxo-2H-pyridin-1-yl)-phenylcarbamoyl]-pyrrolidine-1-carboxylic acid tert-butyl ester, (2S,4S)-4-[(5-Chloro-thiophene-2-carbonyl)-amino]-1-methyl-pyrrolidine-2-carboxylic acid[2-cyano-4-(3-oxo-morpholin-4-yl)-phenyl]-amide, (S)-4-[(5-Chloro-thiophene-2-carbonyl)-amino]-pyrrolidine-2-carboxylic acid[2-cyano-4-(2-oxo-2H-pyridin-1-yl)-phenyl]-amide trifluoro-acetate, and (S)-4-[(5-Chloro-thiophene-2-carbonyl)-amino]-1-methyl-pyrrolidine-2-carboxylic acid [2-cyano-4-(2-oxo-2H-pyridin-1-yl)-phenyl]-amide.

17. A pharmaceutical composition comprising a compound according to claim 1 and a pharmaceutically acceptable excipient.

* * * * *